US012564579B2

(12) United States Patent
Berman et al.

(10) Patent No.: US 12,564,579 B2
(45) Date of Patent: Mar. 3, 2026

(54) TOPICAL FORMULATIONS OF (1S)-1-PHENYL-2-PYRIDIN-2-YLETHANAMINE

(71) Applicant: Biohaven Therapeutics Ltd., New Haven, CT (US)

(72) Inventors: Robert Berman, New Haven, CT (US); Rajesh Kumar, Skillman, NJ (US); Charles M. Conway, Cheshire, CT (US); Mary K. Donohue, Wallingford, CT (US); Ajaya Kumar Reka, Princeton Junction, NJ (US)

(73) Assignee: Biohaven Therapeutics Ltd., Tortola (VG)

( * ) Notice: Subject to any disclaimer, the term of this patent is extended or adjusted under 35 U.S.C. 154(b) by 538 days.

(21) Appl. No.: 17/923,585

(22) PCT Filed: Jun. 23, 2021

(86) PCT No.: PCT/US2021/038564

§ 371 (c)(1),
(2) Date: Nov. 6, 2022

(87) PCT Pub. No.: WO2021/262779

PCT Pub. Date: Dec. 30, 2021

(65) Prior Publication Data

US 2023/0190719 A1 Jun. 22, 2023

Related U.S. Application Data

(60) Provisional application No. 63/043,075, filed on Jun. 23, 2020.

(51) Int. Cl.

| | |
|---|---|
| ***A61K 31/4402*** | (2006.01) |
| ***A61K 9/00*** | (2006.01) |
| ***A61K 45/06*** | (2006.01) |
| ***A61K 47/44*** | (2017.01) |

(52) U.S. Cl.
CPC ........ *A61K 31/4402* (2013.01); *A61K 9/0014* (2013.01); *A61K 45/06* (2013.01); *A61K 47/44* (2013.01)

(58) Field of Classification Search
CPC .. A61K 31/4402; A61K 9/0014; A61K 45/06; A61K 47/44
See application file for complete search history.

(56) References Cited

U.S. PATENT DOCUMENTS

2004/0082543 A1* 4/2004 Cheung .................. A61P 25/02 514/249
2016/0280647 A1 9/2016 Nordvall et al.

FOREIGN PATENT DOCUMENTS

WO 1993020052 A1 10/1993
WO WO-9320052 A1 * 10/1993 ............. A61P 25/28
WO 2018098344 A1 5/2018
WO 2020041329 A1 2/2020

OTHER PUBLICATIONS

Sanacora, et al.; Molecular Psychiatry, v19, pp. 978-985; 2014 (Year: 2014).*
International Search Report dated Oct. 1, 2021 issued for International Application No. PCT/US2021/038564 (2 pages).
Written Opinion dated Sep. 1, 2021 issued for International Application No. PCT/US2021/038564 (11 pages).
International Preliminary Report on Patentability dated Dec. 13, 2022 issued for International Application No. PCT/US2021/038564 (12 pages).

* cited by examiner

*Primary Examiner* — Jeffrey S Lundgren
*Assistant Examiner* — W. Justin Youngblood

(57) ABSTRACT

Provided is a pharmaceutical formulation including (1S)-1-phenyl-2-pyridin-2-ylethanamine, a pharmaceutically acceptable salt thereof, a solvate thereof, or a prodrug thereof; and a pharmaceutically acceptable topical carrier. Also provided is a method for treating neuropathic pain by administering to a patient in need of such treatment a therapeutically effective amount of the pharmaceutical formulation.

15 Claims, No Drawings

TOPICAL FORMULATIONS OF (1S)-1-PHENYL-2-PYRIDIN-2-YLETHANAMINE

CROSS-REFERENCE TO RELATED APPLICATIONS

This application is a national stage application under 35 U.S.C. § 371 of International Application No. PCT/US2021/038564, Jun. 23, 2021, claims priority to U.S. Provisional Application No. 63/043,075 filed Jun. 23, 2020 and all the benefits accruing therefrom under 35 U.S.C. § 119, the content of which is incorporated herein in its entirety by reference.

FIELD OF THE INVENTION

Embodiments of the present invention relate to methods and compositions for the topical treatment of neuropathic pain. Particularly, embodiments of the present invention relate to topical formulations and methods for local delivery of (1S)-1-phenyl-2-pyridin-2-ylethanamine, its pharmaceutically acceptable salts, solvates, and prodrugs in a topical vehicle that limits systemic penetration of the active (1S)-1-phenyl-2-pyridin-2-ylethanamine while providing effective relief from the symptoms of neuropathic pain.

BACKGROUND OF THE INVENTION

Neuropathic pain is caused by damage or injury to the nerves that transfer information between the brain and spinal cord from the skin, muscles and other parts of the body. The pain is usually described as a burning sensation and affected areas are often sensitive to the touch. Symptoms of neuropathic pain may include excruciating pain, pins and needles, difficulty correctly sensing temperatures and numbness.

Common causes of neuropathic pain include nerve pressure or nerve damage after trauma or surgery, infections, cancer, vascular malformations, alcoholism, neurological conditions such as multiple sclerosis and metabolic conditions such as diabetes. Neuropathic pain may also be a side effect of certain medications. Occasionally though, no identifiable cause is found which can be distressing for the individual experiencing the pain. Chronic neuropathic pain is very common and may be related to an underlying health condition such as cancer or diabetic neuropathy, or it could be related to treatments such as chemotherapy.

The primary goals of treatment for neuropathic pain are to manage the pain as much as possible and to minimize the negative side effects of the treatment. However, regular painkillers such as non-steroidal anti-inflammatory drugs or NSAIDs (for example ibuprofen, aspirin, and paracetamol) are usually not effective for neuropathic pain.

There were sporadic reports of using 2-(2-chlorophenyl)-2-(methylamino)cyclohexanone (ketamine) for treating neuropathic pain. (1S)-1-phenyl-2-pyridin-2-ylethanamine (lanicemine) is an N-methyl-D-aspartate (NMDA) receptor antagonist, which was in the development for treatment of severe and treatment-resistant depression. Lanicemine differs from ketamine in that it is a low-trapping NMDA receptor antagonist, showing similar rapid-acting antidepressant effects in clinical trials but with little or no psychotomimetic side effects. However, lanicemine did not meet study endpoints, so its development was terminated by the clinical trials sponsor. No clinical studies of lanicemine as a pain reliever has been reported to date.

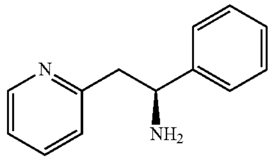

Lanicemine

There remains a need in the art for effective treatments for neuropathies and other neuropathic pains, particularly for treatments that may act at or near the site of pain that minimize the potential for side effects.

SUMMARY OF THE INVENTION

Embodiments of the present invention are directed to topical formulations including (1S)-1-phenyl-2-pyridin-2-ylethanamine as a principal active ingredient.

In an embodiment, a pharmaceutical formulation for topical application is provided. The formulation includes (1S)-1-phenyl-2-pyridin-2-ylethanamine, a pharmaceutically acceptable salt thereof, a solvate thereof, or a prodrug thereof; and a pharmaceutically acceptable topical carrier.

In another embodiment, a method for treating neuropathic pain in a patient in need of such treatment is provided. The method includes administering a therapeutically effective amount of the above pharmaceutical formulation.

DETAILED DESCRIPTION OF THE INVENTION

The following detailed description is provided to aid those skilled in the art in practicing embodiments of the present invention. Exemplary embodiments will hereinafter be described in detail. However, these embodiments are only exemplary, and the present disclosure is not limited thereto but rather is defined by the scope of the appended claims. Those of ordinary skill in the art may make modifications and variations in the embodiments described herein without departing from the spirit or scope of the present disclosure.

Accordingly, the embodiments are merely described below, by referring to structures and schemes, to explain aspects of the present description. As used herein, the term "and/or" includes any and all combinations of one or more of the associated listed items. The term "or" means "and/or." Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

It is understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all technical and scientific terms used herein have the same meaning as commonly understood by one of ordinary skill in the art to which this disclosure belongs. The terminology used in the description is for describing particular embodiments only and is not intended to be limiting. It will be further understood that the terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing embodiments of the present invention.

The articles "a" and "an" refer to one or to more than one (i.e., to at least one) of the grammatical object of the article unless the context clearly indicates otherwise. By way of example, "an element" means one element or more than one element.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

As used herein, when specific definition is not otherwise provided, the term "substituted" refers to a group substituted with deuterium, a halogen (—F, —Cl, —Br, —I), a hydroxy group (—OH), an amino group ($—NH_2$), a carboxyl group ($—CO_2H$), a substituted or unsubstituted C1-C10 amine group, a nitro group ($—NO_2$), a C1-C10 alkyl group, a C3-C10 cycloalkyl group, a C6-C12 aryl group, a C1-C10 alkoxy group, a C1 to C10 trifluoroalkyl group such as a trifluoromethyl group ($—CF_3$) and the like, or a cyano group (—CN) instead of at least one hydrogen of a substituting group or compound.

Additional aspects will be set forth in part in the description which follows and, in part, will be apparent from the description.

The starting materials useful for making the pharmaceutical formulations, according to embodiments of the present invention, are readily commercially available or can be prepared by those skilled in the art.

Principal Active Ingredients

The principal active ingredient of the formulation, according to embodiments of the present invention, includes (1S)-1-phenyl-2-pyridin-2-ylethanamine, a pharmaceutically acceptable salt thereof, a solvate thereof, or a prodrug thereof.

In an embodiment, the active ingredient may be (1S)-1-phenyl-2-pyridin-2-ylethanamine, which may be obtained commercially, or may be prepared according to a published procedure. See PCT Patent Publication WO 93/20052 describing synthesis of (1S)-1-phenyl-2-pyridin-2-ylethanamine free base and (1S)-1-phenyl-2-pyridin-2-ylethanamine dihydrochloride salt.

In another embodiment, the active ingredient may be a pharmaceutically acceptable salt of (1S)-1-phenyl-2-pyridin-2-ylethanamine or a solvate of the salt. Pharmaceutically acceptable salts are non-toxic acid addition salts or metal complexes that are commonly used in the pharmaceutical industry. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts of amines and other types of compounds, are well-known in the art. For example, S. M. Berge, et al. describe pharmaceutically acceptable salts in detail in *J. Pharmaceutical Sciences,* 1977, 66, 1-19. The salts may be prepared in situ during the final isolation and purification of the compounds of the invention, or separately by reacting a free base or free acid function with a suitable reagent, as described generally below. For example, a free base function may be reacted with a suitable acid. Furthermore, where the compounds of the invention carry an acidic moiety, suitable pharmaceutically acceptable salts thereof may include metal salts such as alkali metal salts, e.g., sodium or potassium salts; and alkaline earth metal salts, e.g., calcium or magnesium salts. Examples of pharmaceutically acceptable, non-toxic acid addition salts are salts of an amino group formed with inorganic acids such as hydrochloric acid, hydrobromic acid, phosphoric acid, sulfuric acid, or perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

In an embodiment, the pharmaceutically acceptable salt may be a salt of a C1-C30 carboxylic acid having formula $R_1—CO_2H$, wherein $R_1$ is a lipophilic moiety. The C1-C30 carboxylic acid may be unsubstituted or substituted. The pharmaceutically acceptable salt may be a salt of a C1-C5 (short-chain) carboxylic acid, a salt of a C6-C12 (medium-chain) carboxylic acid, a salt of a C13-C21 (long-chain) carboxylic acid, or a salt of a C22-C30 (very long-chain) carboxylic acid. The C1-C30 carboxylic acid may be linear (unbranched) or branched.

The C1-C30 carboxylic acid may be a naturally occurring fatty acid, which may be saturated or unsaturated. As used herein, the term "saturated fatty acid" refers to a C1-C30 carboxylic acid containing no elements of unsaturation (i.e., no double bond or triple bond), and the term "unsaturated fatty acid" refers to a C1-C30 carboxylic acid containing at least one double bond, wherein the at least one bond may have either cis- or trans-configuration.

Examples of saturated fatty acids include, but are not limited to, caprylic acid (octanoic acid), capric acid (decanoic acid), lauric acid (dodecanoic acid), stearic acid (octadecanoic acid), arachidic acid (eicosanoic acid), behenic acid (docosanoic acid), lignoceric acid (tetracosanoic acid), or cerotic acid (hexacosanoic acid).

Examples of cis-unsaturated fatty acids include, but are not limited to, myristoleic acid (cis-tetradec-9-enoic acid), palmitoleic acid (cis-hexadec-9-enoic acid), sapienic acid (cis-hexadec-6-enoic acid), oleic acid (cis-octadec-9-enoic acid), linoleic acid (cis, cis-octadeca-9, 12-dienoic acid), α-linoleic acid (cis, cis, cis-octadeca-9, 12, 15-trienoic acid), arachidonic acid (cis, cis, cis, cis-eicosa-5, 8, 11, 14-tetraenoic acid), eicosapentaenoic acid (cis, cis, cis, cis, cis-eicosa-5, 8, 11, 14, 17-pentaenoic acid), erusic acid (cis-docosa-13-enoic acid), or docosahexaenoic acid (cis, cis, cis, cis, cis, cis-docosa-4, 7, 10, 13, 16, 19-hexenoic acid).

Examples of trans-unsaturated fatty acid include, but are not limited to, elaidic acid (trans-octadec-9-enoic acid), vaccenic acid (trans-octadec-11-enoic acid), or linoelaedic acid (trans, trans-octadeca-9, 12-dienoic acid).

The naturally occurring fatty acid may be an unbranched chain carboxylic acid including an odd number of carbon atoms, such as pentadecanoic acid or a heptadecanoic acid. However, the naturally occurring fatty acid may also be an unbranched chain carboxylic acid including an even number of carbon atoms.

The naturally occurring fatty acid may be an omega-3 fatty acid. Examples of the omega-3 fatty acids include, but are not limited to, α-linoleic acid, stearidonic acid (cis, cis, cis, cis-octadeca-5, 6, 12, 15-tetraenoic acid), eicosatetraenoic acid (cis, cis, cis, cis-octadeca-8, 11, 14, 17-tetraenoic acid), eicosapentaenoic acid, clupanodonic acid (cis, cis, cis, cis, cis-docosa-7, 10, 13, 16, 19-pentaenoic acid), tetracosapentaenoic acid (cis, cis, cis, cis, cis-tetracosa-6, 9, 12, 15, 18-pentaenoic acid), tetracosahexaenoic acid (cis, cis, cis, cis, cis-tetracosa-9, 12, 15, 18, 21-hexaenoic acid), or docosahexaenoic acid.

The naturally occurring fatty acid may be an omega-6 fatty acid. Examples of the omega-6 fatty acids include, but are not limited to, linoleic acid, γ-linoleic acid (cis, cis, cis-octadeca-6, 9, 12-trienoic acid), dihomo-γ-linoleic acid (cis, cis, cis-octadeca-8, 11, 14-trienoic acid), arachidonic acid, tetracosatetraenoic acid (cis, cis, cis, cis-eicosa-9, 12, 15, 18-tetraenoic acid), tetracosapentaenoic acid (cis, cis, cis, cis, cis-tetracosa-9, 12, 15, 18, 21-pentaenoic acid), or osbond acid (cis, cis, cis, cis, cis-docosa-4, 7, 10, 13, 16-pentaenoic acid).

Fatty acid salts of (1S)-1-phenyl-2-pyridin-2-ylethanamine may possess improved stability and enhanced permeability over (1S)-1-phenyl-2-pyridin-2-ylethanamine free base, and thus, may be desirable for topical formulations, according to embodiments of the present invention.

In another embodiment, the active ingredient may be a solvate of (1S)-1-phenyl-2-pyridin-2-ylethanamine. Solvates are compounds formed by solvation, which is the combination of solvent molecules with molecules or ions of the solute. Solvation is an interaction of a solute with the solvent, which leads to stabilization of the solute species in the solution. One may also refer to the solvated state, whereby an ion in a solution is complexed by solvent molecules. The difference in the physical properties of different solvates and polymorph forms thereof results from different orientation and intermolecular interactions of adjacent molecules in the solid. Polymorphic forms of compounds or solvates can be distinguished by X-ray diffraction and by other methods such as, infrared spectroscopy or Raman spectroscopy.

Upon contact with an appropriate solvent, (1S)-1-phenyl-2-pyridin-2-ylethanamine may form a hydrate with water, a solvate with a C1-C30 alcohol (e.g., methanol, ethanol, propanol, etc.); an adduct with a C1-C30 amino compound (e.g., ammonia, methylamine, ethylamine, etc.); an adduct with a C1-C30 carboxylic acid (e.g., formic acid, acetic acid, etc.); complexes with ethanolamine, quinoline, amino acids, and the like. The solvate with a C1-30 alcohol may be a solvate with a C1-C20 alcohol, a solvate with a C1-C10 alcohol, or a solvate with a C1-C5 alcohol. Typically, hydrates and solvates of (1S)-1-phenyl-2-pyridin-2-ylethanamine are formed during recrystallization. Theoretically, any compound containing a moiety having an active hydrogen atom (e.g., —OH, —NH, —SH, —PH) or a moiety having an unshared pair of electrons (e.g., O, N, S, P) may form a solvate with (1S)-1-phenyl-2-pyridin-2-ylethanamine.

In another embodiment, the active ingredient may be a prodrug of (1S)-1-phenyl-2-pyridin-2-ylethanamine. Skin as a route for drug delivery has been extensively investigated, but due to the predominant barrier function of stratum corneum in skin, the clinical application of drug delivery via skin may be limited. One strategy to solve this problem of skin drug permeation is the use of a prodrug of (1S)-1-phenyl-2-pyridin-2-ylethanamine. Prodrugs are inactive compounds which are metabolized either chemically or enzymatically in a controlled or predictable manner to its parent active drug. Prodrugs can enhance dermal/transdermal drug delivery via different mechanisms, including increased skin partitioning, increased aqueous solubility, and reduced crystallization, etc. Besides the prodrug itself, the optimization of vehicle is important as well. The prodrug partitioning between skin and vehicle as well as prodrug-vehicle interaction may influence the enhancing efficacy on skin permeation. For detailed review of prodrug strategy for enhancing drug delivery via skin, see Fang J-Y. et al. *Curr. Drug. Discov. Technol.* 2006, 3(3), 211-224.

In an embodiment, the prodrug of (1S)-1-phenyl-2-pyridin-2-ylethanamine may be represented by the following Chemical Formula 1:

Chemical Formula 1

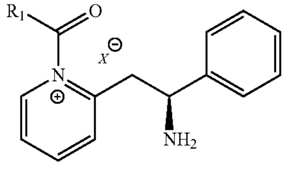

In Chemical Formula 1, $R_1$ is a lipophilic moiety derived from a C1-C30 carboxylic acid having formula $R_1$—$CO_2H$ that has been described above in connection with a pharmaceutically acceptable salt of (1S)-1-phenyl-2-pyridin-2-ylethanamine, and X is a moiety derived from an inorganic or organic acid.

In Chemical Formula 1, X may be a halogen or a residue of a nitrogen-containing, sulfur-containing, or phosphorus-containing inorganic or organic acid.

The prodrugs having Chemical Formula 1 may be prepared by reacting (1S)-1-phenyl-2-pyridin-2-ylethanamine with a C1-C30 alkanoyl halide having formula $R_1$—$CO_2X$, wherein X is a halogen, for example, fluorine, chlorine, bromine, or iodine. If desired, group X may be subsequently exchanged for another anionic moiety. A protection of the amino group of (1S)-1-phenyl-2-pyridin-2-ylethanamine may be required prior to conducting a reaction of (1S)-1-phenyl-2-pyridin-2-ylethanamine with $R_1$—$CO_2X$. The protecting group may be subsequently removed to provide the desired prodrug.

The prodrug having Chemical Formula 1 may be useful for preparation of topical formulations. Once applied on and permeated through the skin, the prodrug may undergo enzymatic cleavage across the bond connecting the carbon atom of the carbonyl group and the nitrogen atom of the pyridine ring. The enzymes involved in the carbon-nitrogen bond cleavage are esterases that are distributed throughout the human and animal skin layers.

In another embodiment, the prodrug of (1S)-1-phenyl-2-pyridin-2-ylethanamine may be represented by the following Chemical Formula 2:

Chemical Formula 2

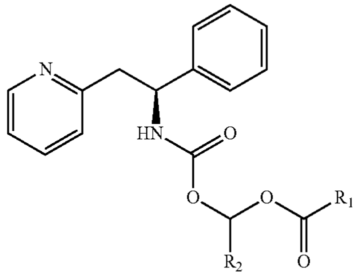

In Chemical Formula 2, $R_1$ is a lipophilic moiety derived from a C1-C30 carboxylic acid having formula $R_1$—$CO_2H$ that has been described above in connection with a pharmaceutically acceptable salt of (1S)-1-phenyl-2-pyridin-2-ylethanamine, $R_2$ is H or a C1-C10 unsubstituted or substituted hydrocarbon group, and X is a moiety derived from an inorganic or organic acid.

In Chemical Formula 2, $R_1$ may be a lipophilic moiety derived from a C8-C30 carboxylic acid having formula $R_1$—$CO_2H$. $R_2$ may be a C1-C10 alkyl group, a C1-C10 alkenyl group, or a C1-C10 alkynyl group. X may be a halogen or a residue of a nitrogen-containing, sulfur-containing, or phosphorus-containing inorganic or organic acid.

The prodrugs having Chemical Formula 2 may be prepared according to a process described in PCT Patent Publication WO 2015/067923.

The prodrug having Chemical Formula 2 may be useful for preparation of topical formulations. Once applied on and permeated through the skin, the prodrug may undergo enzymatic cleavage across the bond connecting the carbon atom of the carbonyl group and the nitrogen atom of the pyridine ring. The enzymes involved in the carbon-nitrogen bond cleavage are esterases that are distributed throughout the human and animal skin layers.

Additional Active Ingredients

Local Analgecics

The formulations described herein may include one or more local analgesics. As used herein, the term "local analgesic" refers to any drug that reduces or eliminates pain without causing numbness or any drug that provides a regional blockage of nociceptive pathways (afferent and/or efferent). The local analgesic may be any local analgesic known or to be developed. When present in the formulation, the amount of local analgesic may be from about 0.1% to about 10% by weight of the total formulation weight, for example, about 1% to 5% by weight of the total formulation weight.

Examples of local analgesics are non-steroidal anti-inflammatory drugs ("NSAIDs"). See, for example, *Transdermal and Topical Drug Delivery Systems* (Tapash K. Ghosh et al. eds., 1997, pp. 87-93). NSAIDs provide analgesic and antipyretic (fever-reducing) effects, and, in higher doses, anti-inflammatory effects. The term "non-steroidal" distinguishes these drugs from steroids, which, among a broad range of other effects, have a similar eicosanoid-depressing, anti-inflammatory action. As analgesics, NSAIDs are unusual in that they are non-narcotic. NSAIDs are usually indicated for the treatment of acute or chronic conditions where pain and inflammation are present. Common NSAID classification groups include: salicylates (e.g., aspirin (acetylsalicylic acid), diflunisal, and salsalate, propionic acid derivatives (e.g., ibuprofen, dexibuprofen, naproxen, fenoprofen, ketoprofen, dexketoprofen, flurbiprofen, oxaprozin, and loxoprofen), acetic acid derivatives (e.g., indomethacin, tolmetin, sulindac, etodolac, ketorolac, diclofenac, and nabumetone), enolic acid derivatives (e.g., piroxicam, meloxicam, tenoxicam, droxicam, lornoxicam, and isoxicam), fenamic acid derivatives (e.g., mefenamic acid, meclofenamic acid, flufenamic acid, and tolfenamic acid), selective COX-2 inhibitors (e.g., celecoxib, rofecoxib, valdecoxib, parecoxib, lumiracoxib, etoricoxib, firocoxib, and paracetamol), and sulphonanilides (e.g., nimesulide), along with other compounds that do not fall into one of these categories (e.g., licofelone, lysine clonixinate, and hyperforin, and calcitriol). NSAIDs within a group tend to have similar characteristics and tolerability. There appears to be little difference in clinical efficacy among the NSAIDs when used at equivalent doses. Rather, differences among compounds usually relate to dosing regimens, route of administration, and tolerability profile.

Opioids, such as morphine, are known to have local analgesic properties when topically administered in mammals. See, for example, U.S. Pat. No. 5,948,389 and Christoph Stein et al. *Pain* 1997, 71, 119-121.

As used herein, the term "opioid" refers to all agonists and antagonists of opioid receptors, such as mu (μ), kappa (κ), and delta (δ) opioid receptors and subtypes thereof. For a discussion of opioid receptors and subtypes, see Goodman & Gilman's the *Pharmacological Basis of Therapeutics* 521-525 (Joel G. Hardman et al. eds., 9th ed. 20 1996). The opioid can be any opioid receptor agonist or antagonist known or to be developed. The opioids may interact with the μ-opioid receptor, the κ-opioid receptor, or both. The opioid may be an opioid-receptor agonist.

Examples of suitable opioids include, but are not limited to, alfentanil, allylprodine, alphaprodine, anileridine, benzylmorphine, benzitramide, nor-binaltorphimine, bremazocine, buprenorphine, butorphanol, clonitazene, codeine, CTOP, DAMGO, desomorphine, dextromoramide, dezocine, diampromide, dihydrocodeine, dihydrocodeine enol acetate, dihydromorphine, dimenoxadol, dimepheptanol, dimethylthiambutene, dioxaphetyl butyrate, dipipanone, diprenorphine, DPDPE, eptazocine, ethoheptazine, ethylketocyclazocine, ethylmethylthiambutene, etonitazene, etorphine, fentanyl, hydrocodone, hydromorphone, hydroxypethidine, isomethadone, ketobemidone, levorphanol, lofentanil, loperamide, meperidine, meptazinol, metazocaine, methadone, metopon, morphine, myrophine, nalbuphine, naltrindole, benzoylhydrazone, naltrexone, narceine, nicomorphine, norlevorphanol, normethadone, nornorphine, norpipanone, opium, oxycodone, oxymorphone, papavereturn, papaverine, pentazocine, phenadoxone, phenazocine, phenoperidine, piminodine, pirtramide, proheptazine, promedol, propiram, propoxyphene, remifentanil, spiradoline, sufentanil, tilidine, U50,488, and U69,593, amiphenazole, cyclazocine, levallorphan, nalmefene, nalorphine, naloxone, and naltrexone or pharmaceutically-acceptable salts thereof, or combinations thereof.

Examples of peptide opioids include, but are not limited to, Tyr-Gly-Gly-Phe-Leu ([Leu 5]enkephalin), Tyr-Gly-Gly-Phe-Met ([Met 5]enkephalin), Tyr-Gly-Gly-Phe-Leu-Arg-Arg-Ile-Arg-Pro-Lys-Leu-Lys-Trp-Asp-Asn-Gln (Dynorphin A), Tyr-Gly-Gly-Phe-Leu-Arg-Arg-Gln-Phe-Lys-Val-Val-Thr (Dynorphin B), Tyr-Gly-Gly-Phe-Leu-Arg-Lys-Tyr-Pro-Lys (α-Neoendorphin), Tyr-Gly-Gly-Phe-Leu-Arg-Lsy-Tyr-Pro (β-Neoendorphin), Tyr-Gly-Gly-Phe-Met-Thr-Ser-Glu-Lys-Ser-Gln-Thr-Pro-Leu-Val-Thr-Leu-Phe-Lys-Asn-Ala-Ila-Ile-Lsy-Asn-Ala-Tyr-Lys-Lys-Gly-Glu ((Ph-Endorphin), [D-Ala 2, MePhe 4 Gly(ol) 5]enkephalin (DAMGO), [D-Pen 2, D-Pen 5]enkephalin (DPDPE), [D-Ser 2, Leu 5]enkephalin-Thr 6 (DSLET), [D-Ala 2, D-Leu 5]enkephalin (DADL), D-Phe-Cys-Tyr-D-Trp-Orn-Thr-Pen-Thr-NH 2 (CTOP), [D-Ala 2, N-MePhe 4, Met(O) 5-ol]enkephalin (FK-33824), Tyr-D-Ala-Phe-Asp-Val-Val-Gly-NH 2 ([D-Ala 2]Deltorphin 1), Tyr-D-Ala-Phe-Glu-Val-Val-Gly-NH 2 ([D-Ala 2 Glu 4]Deltorphin (Deltorphin II)), Tyr-Pro-Phe-Pro-NH 2 (Morphiceptin), Tyr-Pro-MePhe-D-Pro-NH 2 (PL017), [D-Ala 2, Leu 5, Cys 6]enkephalin (DALCE) or pharmaceutically-acceptable salts thereof, or mixtures thereof. Opioids may include morphine, loperamide, and loperamide derivatives such as those disclosed in U.S. Pat. Nos. 5,763,445; 5,981,513; 5,869,521; 5,744,458; 5,760,023; 5,798,093; 5,849,762; 5,811,078; 6,004,964; 5,962,477; 5,688,955; 5,888,494; 5,646,151; and 5,667,773 or pharmaceutically-acceptable salts thereof, or combinations thereof.

Other examples of local analgesics include anticholinergic agents, an example of which are tricyclic antidepressants such as amitriptylline described in U.S. Pat. No. 3,205,264. The mechanism of action of amitriptylline is presumed to be due to the anticholinergic action of the tricyclic antidepressant. Once the antidepressant (or one of the other anticholinergics) passes through the dermis it acts by blocking acetylcholine, a neurotransmitter. This prevents the transmission of impulses in the A-delta and C pain fibers, thereby resulting in pain relief.

Local analgesics may also be included in the formulations, according to embodiments of the present invention, to prolong the local analgesic effect, such as, a glucocorticosteroid (see, for example, U.S. Pat. No. 5,922,340) or a vasoconstrictor, such as a catecholamine.

Local Anesthetics

The formulations, according to embodiments of the present invention, may include one or more additional local anesthetics. As used herein, the term "local anesthetic" refers to any compound or composition that reduces or eliminates pain by providing local numbness. The local anesthetic may be any local anesthetic known or to be developed. When present in the formulation, the amount of local anesthetic may be from about 0.1% to about 10% by weight of the total formulation weight.

Examples of local anesthetics suitable for use in the formulation include sodium channel blockers. Sodium channel blockers, such as lidocaine prevent the generation and conduction of nerve impulses by decreasing or preventing the large transient increase in the permeability of excitable membranes to $Na^+$. Examples of sodium channel blockers include, but are not limited to, ambucaine, amolanone, amylcaine, benoxinate, benzocaine, etoxycaine, biphenamine, bupivacaine, butacaine, butamben, butanilicaine, butethamine, butoxycaine, carticaine, chloroprocaine, cocaethylene, cocaine, cyclomethycaine, dibucaine, dimethisoquin, dimethocaine, diperodon, dyclonine, ecogonidine, ecogonine, euprocin, fenalcomine, formocaine, hexylcaine, hydroxyteteracaine, isobutyl p-aminobenzoate, leucinocaine, levoxadrol, lidocaine, mepivacaine, meprylcaine, metabutoxycaine, methyl chloride, myrtecaine, naepaine, octacaine, orthocaine, oxethazaine, parenthoxycaine, phenacaine, phenol, piperocaine, piridocaine, polidocanol, pramoxine, prilocalne, procaine, propanocaine, proparacaine, propipocaine, propoxycaine, pseudococaine, pyrrocaine, ropivacaine, salicyl alcohol, tetracaine, tolycaine, trimecaine, zolarmine, or pharmaceutically acceptable salts thereof, or combinations thereof.

Medicinal Agents

The formulations described herein may include a medicinal agent or a pharmaceutically acceptable salt thereof. As used herein, the term "medicinal agent" refers to any compound or composition that produces a therapeutic effect, other than a local analgesic or anesthetic. One of ordinary skill in the art may choose a medicinal agent to incorporate into the formulation and its appropriate concentration depending on the indication and desired effect. Examples of medicinal agents include, but not limited to, antifungals such as ciclopirox, chloroxylenol, triacetin, sulconazole, nystatin, undecylenic acid, tolnaftate, miconizole, clotrimazole, oxiconazole, griseofulvin, econazole, ketoconazole, and amphotericin B; antibiotics, such as mupirocin, erthromycin, clindamycin, gentamicin, polymyxin, bacitracin, and silver sulfadiazine; antiseptics, such as iodine, povidine-iodine, benzalkonium chloride, benzoic acid, chlorhexidine, nitrofurazone, benzoyl peroxide, hydrogen peroxide, hexachlorophene, phenol, resorcinol, and cetylpyridinium chloride; and anti-inflammatories, such as hydrocortisone, prednisone, triamcilolone, betamethasone, dexamethasone.

Neuroprotective Agents

The formulations described herein may include a neuroprotective agents, which is a compound or composition administered to prevent or slow the damage or loss of neurons. Several neuroprotective agents have been tested for the prevention of chemotherapy induced peripheral neuropathy (CIPN) with varying results (Pachman et al. *Clinical Pharmacology & Therapeutics,* 2011, 90, 377-386); these include, without limitation, calcium, magnesium, glutathione, glutamine, carbamaepine, oxycarbazepine, vitamin E, erythropoietin, allopregnanolone, valproate, alpha-lipoic acid, acetyl-L-carnitine and combinations, such as calcium and magnesium infusions.

Excipients and Formulations

The formulations, according to embodiments of the present invention, includes a therapeutically effective amount of the active ingredient in a topical vehicle that limits penetration of (1S)-1-phenyl-2-pyridin-2-ylethanamine generally to the skin, particularly to the epidermis, dermis and the dermatomes, or alternatively, minimizes systemic penetration. The formulation typically includes (1S)-1-phenyl-2- pyridin-2-ylethanamine in amounts sufficient to treat neuropathy when the formulation is administered topically in a physiologically acceptable vehicle or carrier. The formulations in which the compositions described herein are incorporated may be prepared in any of a variety of dosage forms, including solutions, suspensions, ointments, and solid inserts. Examples are creams, lotions, gels, ointments, suppositories, sprays, foams, liniments, aerosols, buccal and sublingual tablets, various passive and active topical devices for absorption through the skin and mucous membranes, including topical applications, and the like.

Skin Retardants

The topical administration is designed to maximize drug delivery through the stratum corneum and into the epidermis or dermis or dermatome to minimize absorption into the circulatory system. Thus, certain excipients may be used in the topical formulations disclosed herein to prevent the passage of active ingredients or excipients into the lower skin layers. These so-called skin retardants have been developed for certain over-the-counter skin formulations, such as sunscreens, where the site of action is restricted to the skin surface or upper skin layers. Research in the area of permeation enhancement or retardation is yielding valuable insights into the structure-activity relationships of enhancers as well as retardants including such compounds as ketorolac stearate, aminocaprolactam analogues, dicarboxylic acid ester, sodium citrate, and the like. See, e.g., Asbill C. S. and Michniak B. B., *Pharm Sci & Tech Today,* 2000, 3, 36-41; Kaushik D. et al., *Exp Opin Drug Del* 2008, 5, 517-529; Trommer H. and Neubert R. H. H. *Skin Pharmacol Physiol* 2006, 19, 106-121; Neubert R et al., *Pharmazeutische Zeitung* 1996, 141 1483-1493; Benson H. A. E., *Curr Drug Del* 2005, 2, 23-33.

Carriers

The formulation may include a dermatologically acceptable carrier. A dermatologically acceptable carrier may be a solid carrier such as alumina, clay, microcrystalline cellulose, silica, or talc; and/or a liquid carrier, for example, water, mixtures of water and water-miscible solvents such as lower alkanols or vegetable oils, and water-soluble ophthalmologically acceptable non-toxic polymers, for example, cellulose derivatives such as methylcellulose. A typical cream or ointment-type carrier for topical application that can be used according to the methods and formulations described herein include a mixture of water, glycerin, propylene glycol, and methylparaben. Topical carriers may also include other conventional emulsifiers and emollients including alginates, glyceryl stearate, PEG-100 stearate, cetyl alcohol, propylparaben, butylparaben, sorbitols, polyethoxylated anhydrosorbitol monostearate (TWEEN®), white petrolatum (VASELINE®), triethanolamine, Emu oil, aloe vera extract, lanolin, cocoa butter, and the like.

The therapeutic agents may also be administered in liposomal formulations that allow therapeutic agents to enter the skin. Such liposomal formulations are described in U.S. Pat. Nos. 5,169,637; 5,000,958; 5,049,388; 4,975,282; 5,194,266; 5,023,087; 5,688,525; 5,874,104; 5,409,704; 5,552,155; 5,356,633; 5,032,582; 4,994,213; and PCT Publication No. WO 96/40061. Examples of other appropriate vehicles are described in U.S. Pat. No. 4,877,805 and EP Publication No. 0586106. Suitable vehicles for embodiments of the present invention may also include mineral oil, petrolatum, polydecene, stearic acid, isopropyl myristate, polyoxyl 40 stearate, stearyl alcohol, or vegetable oil.

Suitable topical carriers are known to the skilled artisan. Standard texts, such as Gennaro, A. R., *Remington: The Science and Practice of Pharmacy,* 21st edition, Lippincott, Williams & Wilkins (2006), J. G., Goodman & Gilman's The Pharmacological Basis of Therapeutics, 10th edition, McGraw-Hill Professional; Shah & Maibach, Topical Drug Bioavailability, *Bioequivalence, and Penetration,* 1st edition, Plenum Pub Corp.; Hillery et al., Drug Delivery and Targeting: For Pharmacists and Pharmaceutical Scientists, Harwood Academic Pub.; Ansel et al., *Pharmaceutical Dosage Forms and Drug Delivery Systems,* 7th edition, Lippincott Williams & Wilkins, can be consulted to prepare suitable compositions for topical administration, without undue experimentation. Suitable dosages can also be determined based upon the text and documents cited herein.

Solvents and Solubilizers

The formulation may include a solvent or solubilizer. Examples of solvents or solubilizers, which may include the pharmaceutically acceptable vehicle of this formulation, include one or more of materials such as glycerin, propylene glycol, isopropanol, ethanol, a variety of polyethylene glycols, block copolymers of ethylene glycol and propylene glycol, acetylated monoglycerides, lanolin, mineral oil, water, aqueous buffers and the like.

The formulation may include a water-miscible alkylene glycol. Suitable water-miscible alkylene glycols are polyhydric alcohols such as glycerol, dipropylene glycol, polyethylene glycol, propylene carbonate, propylene glycol, butylene glycol, pentylene glycol, hexylene glycol, and the like. Propylene glycol is the preferred water-miscible alkylene glycol.

Propylene glycol is a colorless, nearly odorless, clear, viscous liquid. Propylene glycol acts as a solvent and antimicrobial in the present formulation. The freezing point of water is depressed when mixed with propylene glycol due to increased opportunity for hydrogen bonding. The total propylene glycol concentration may not exceed 12% by weight of the total formulation weight to avoid a negative effect on permeation and physical stability.

Lipophilic Components

The formulation may include a lipophilic component. The lipophilic component in the formulation, according to embodiments of the present invention, may be any water insoluble (hydrophobic) organic material or mixture of materials that can form a stable emulsion including (1S)-1-phenyl-2-pyridin-2-ylethanamine, a pharmaceutically acceptable salt thereof, a solvate thereof, or a prodrug thereof that is suitable for intradermal administration. The lipophilic component may be included in about 15% to about 40% by weight, for example, about 20% by weight of the total formulation weight.

Suitable lipophilic components are known in the art and include, but are not limited to, vegetable, nut, and seed oils, such as almond oil, castor oil, coconut oil, corn oil, cotton seed oil, jojoba oil, linseed oil, grape seed oil, rape seed oil, mustard oil, olive oil, palm and palm kernel oil, peanut oil, safflower oil, sesame oil, soybean oil, sunflower seed oil, crambe oil, wheat germ oil, and cocoa butter; animal oils and fats, such as lanolin, tallow, lard, beef fat, butterfat, mink oil, and fish oils; hydrocarbon and petroleum oils, such as petrolatum, mineral oil, and liquid paraffin; and higher fatty acids such as lauric acid, myristic acid, palmitic acid, stearic acid, behenic acid, oleic acid, 12-hydroxystearic acid, undecylenic acid, tall acid, lanolin fatty acid, isostearic acid, linoleic acid, and linolenic acid, and derivatives thereof.

The lipophilic component may include an emulsifying agent, which is used to stabilize an emulsion and include both a hydrophobic and hydrophilic component in its chemical structure. Emulsifying agents may also aid in the dissolution of ingredients in a solvent in which they would not normally dissolve. Emulsifying agents generally concentrate at and are adsorbed onto the oil:water interface to provide a protective barrier around the dispersed droplets. Exemplary emulsifying agents include tragacanth, triethanolamine oleate, potassium oleate, sodium oleate, sodium lauryl sulfate, sodium dioctyl sulfosuccinate, glyceryl monostearate, and polymers, such as Spans® (e.g., Span® 20, 40, 60, 65, 80, 85), Tweens® (e.g., Tween® 20, 21, 40, 60, 61, 65, 80, 81, 85), PEG 400 Monoleate, PEG 400 monostearate, PEG 400 monolauarate, and PEG-40 hydrogenated castor oil (a polyethylene glycol derivative of castor oil). Emulsifying agents can be classified according to chemical structure or mechanism of action. All emulsifying agents must be chemically stable in the system, inert, and chemically non-reactive with other components of the formulation, and non-toxic and nonirritant. Examples of synthetic emulsifying agents include benzalkonium chloride, benzethonium chloride, alkali soaps (e.g., sodium or potassium oleate), amine soaps (e.g., triethanolamine stearate), detergents (e.g., sodium lauryl sulfate, sodium dioctyl sulfosuccinate, sodium docusate), sorbitan esters (Spans®), polyoxyethylene derivatives of sorbitan esters (Tweens®), or glyceryl esters. Examples of hydrocolloid emulsifying agents include vegetable derivatives (e.g., acacia, tragacanth, agar, pectin, carrageenan, lecithin), animal derivatives (e.g., gelatin, lanolin, cholesterol), semi-synthetic agents (e.g., methylcellulose, carboxymethylcellulose), and synthetic agents (e.g., Carbopols®). Examples of solid particle emulsifying agents include bentonite, veegum, hectorite, magnesium hydroxide, aluminum hydroxide and magnesium trisilicate.

The lipophilic component may include a stiffening agent, which is a hydrophobic material that is a solid at room temperature but melts within the temperature range of about 40° C. to 80° C. to provide a creamy feel to the formulation, according to embodiments of the present invention. The amount of the stiffening agent may be about 1% to about 10% by weight of the total formulation weight. Examples of suitable stiffening agents include, but are not limited to, cetyl alcohol, cetyl esters wax, microcrystalline wax, paraffin, stearyl alcohol, lauryl alcohol, miracle alcohol, cetostearyl alcohol, white wax, yellow wax, bee wax, candelilla wax, cotton wax, carnauba wax, bayberry wax, rice-bran wax. In an embodiment, the stiffening agent may be cetyl alcohol.

The lipophilic component may include a hydrophobic material that facilitates absorption of (1S)-1-phenyl-2-pyridin-2-ylethanamine, a pharmaceutically acceptable salt thereof, a solvate thereof, or a prodrug thereof into the skin, referred to herein as a "lipophilic intradermal-penetration enhancer." The amount of lipophilic-intradermal-penetration enhancer in the formulation may be about 1% to about 99% by weight, for example, about 1% to about 15%, of the total formulation weight. Suitable lipophilic intradermal penetration enhancers include isopropyl myristate, glycerol monolaurate, glycerol monooleate, glycerol monolinoleate, isopropyl isostearate, isopropyl linoleate, isopropyl myristate/fatty acid monoglyceride combination, isopropyl myristate/ethanol/L-lactic acid combination, isopropyl palmitate, methyl acetate, methyl caprate, and methyl laurate.

The lipophilic component may further include a lipophilic solvent, which may include a mixture of one or more aliphatic alcohols (e.g., C2 to C8 monohydric alkanol alcohols) and one or more C8 to C30 aliphatic esters. Alternatively, a lipophilic solvent may be one or more C8 to C30 aliphatic esters. Suitable monohydric alkanol alcohols are C2 and C3 alkanols such as ethanol, propanol, isopropanol, and the like. Isopropyl alcohol and ethyl alcohol are colorless, flammable, chemical compounds. They are miscible in water, alcohol, ether and chloroform. Isopropyl alcohol and ethyl alcohol dissolve a wide range of non-polar compounds. They also evaporate quickly and are relatively non-toxic, compared to alternative solvents. In the present formulation, isopropyl alcohol and ethyl alcohol act as solvent and permeation enhancers. Suitable aliphatic esters are lauryl lactate, propylene glycol laurate, isopropyl myristate, isopropyl palmitate, propylene glycol caprylate, lanolin, and the like. Lauryl lactate, propylene glycol laurate, and isopropyl myristate are the preferred aliphatic esters. Lauryl lactate and propylene glycol laurate are the particularly preferred aliphatic esters. In formulations containing isopropyl myristate, isopropyl myristate can act as a solvent, stabilizer, as well as an emollient.

In some embodiments, the formulation may include 10% to 60% by weight of the one or more aliphatic alcohols (e.g., 10% to 50% by weight, 10% to 40% by weight, 20% to 60% by weight, 20% to 50% by weight, or 20% to 40% by weight of the total formulation weight).

In certain embodiments, the formulation may include 1% to 10% by weight of the one or more aliphatic esters (e.g., 1% to 6% by weight, 2% to 10% by weight, 2% to 6% by weight, 3% to 10% by weight, or 3% to 6% by weight) of the total formulation weight.

The alcohols present in the formulations contribute to skin permeation, wherein the total monohydric alcohol concentration may be 50% or less by weight (e.g., 45% or less by weight, 40% or less by weight, or 35% or less by weight) of the total formulation weight to maintain optimum skin permeation.

Surfactants

The formulations, according to embodiments of the present invention, may include a surfactant to stabilize the emulsion. Surfactants may be cationic, non-ionic, anionic, or amphoteric. For an extensive discussion on surfactants and emulsions, see Gillian M. Eccleston, *Emulsions in Encyclopedia of Pharmaceutical Technology* 5, 137-184 (James C. Swarbrick & James C. Boylan eds. 1988). For use in the formulation, the surfactant may be any intradermally-acceptable hydrophilic or hydrophobic material or mixture of materials capable of stabilizing an oil-in-water type emulsion. One of ordinary skill in the art would be able to choose a suitable surfactant or surfactant mixture based on the hydrophilic-lipophilic balance (HLB) values of the surfactant and the lipophilic component. The amount of the surfactant in the formulation may be about 2% to about 15% by weight, for example, about 10% of the total weight of the formulation.

Examples of anionic surfactants include, but are not limited to, ammonium lauryl sulfate, sodium lauryl sulfate, ammonium laureth sulfate, sodium laureth sulfate, alkyl glyceryl ether sulfonate, triethylamine lauryl sulfate, triethylamine laureth sulfate, triethanolamine lauryl sulfate, triethanolamine laureth sulfate, monoethanolamine lauryl sulfate, monoethanolamine laureth sulfate, diethanolamine lauryl sulfate, diethanolamine laureth sulfate, lauric monoglyceride sodium sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, triethanolamine lauryl sulfate, triethanolamine lauryl sulfate, monoethanolamine cocoyl sulfate, monoethanolamine lauryl sulfate, sodium tridecyl benzene sulfonate, sodium dodecyl benzene sulfonate, sodium and ammonium salts of coconut alkyl triethylene glycol ether sulfate; tallow alkyl triethylene glycol ether sulfate, tallow alkyl hexaoxyethylene sulfate, disodium N-octadecylsulfosuccinate, disodium lauryl sulfosuccinate, diammonium lauryl sulfosuccinate, tetrasodium N-(1,2-dicarboxyethyl)-N-octadecylsulfosuccinate, diamyl ester of sodium sulfosuccinic acid, dihexyl ester of sodium sulfosuccinic acid, dioctyl esters of sodium sulfosuccinic acid, docusate sodium, and combinations thereof.

Examples of non-ionic surfactants include, but are not limited to, polyoxyethylene fatty acid esters, sorbitan esters, cetyl octanoate, cocamide DEA, cocamide MEA, cocamido propyl dimethyl amine oxide, coconut fatty acid diethanol amide, coconut fatty acid monoethanol amide, diglyceryl diisostearate, diglyceryl monoisostearate, diglyceryl monolaurate, diglyceryl monooleate, ethylene glycol distearate, ethylene glycol monostearate, ethoxylated castor oil, glyceryl monoisostearate, glyceryl monolaurate, glyceryl monomyristate, glyceryl monooleate, glyceryl monostearate, glyceryl tricaprylate/caprate, glyceryl triisostearate, glyceryl trioleate, glycol distearate, glycol monostearate, isooctyl stearate, lauramide DEA, lauric acid diethanol amide, lauric acid monoethanol amide, lauric/myristic acid diethanol amide, lauryl dimethyl amine oxide, lauryl/myristyl amide DEA, lauryl/myristyl dimethyl amine oxide, methyl gluceth, methyl glucose sesquistearate, oleamide DEA, PEG-distearate, polyoxyethylene butyl ether, polyoxyethylene cetyl ether, polyoxyethylene lauryl amine, polyoxyethylene lauryl ester, polyoxyethylene lauryl ether, polyoxyethylene nonylphenyl ether, polyoxyethylene octyl ether, polyoxyethylene octylphenyl ether, polyoxyethylene oleyl amine, polyoxyethylene oleyl cetyl ether, polyoxyethylene oleyl ester, polyoxyethylene oleyl ether, polyoxyethylene stearyl amine, polyoxyethylene stearyl ester, polyoxyethylene stearyl ether, polyoxyethylene tallow amine, polyoxyethylene tridecyl ether, propylene glycol monostearate, sorbitan monolaurate, sorbitan monooleate, sorbitan monopalmitate, sorbitan monostearate, sorbitan sesquioleate, sorbitan trioleate, stearamide DEA, stearic acid diethanol amide, stearic acid monoethanol amide, laureth-4, and combinations thereof. Also included are Cremophor RH 40™ (polyoxyl 40 hydrogenated castor oil), Cremophor EL™ (polyoxyl 35 castor oil), Cremophor ELP™ (polyoxyl 35 castor oil), and Solutol HS 15™ (macrogol 15 hydroxystearate), PEG-40 palm kernel oil, PEG-50 hydrogenated castor oil, PEG-60 castor oil, monostearate (and derivatives thereof), glyceryl laurate, glyceryl stearate, glyceryl oleate, glyceryl monooleate, glyceryl monolaurate, sorbitan monooleate, sorbitan monolaurate, sorbitan monopalmitate, sorbitan stearate, nonyl phenols, octyl phenols, caprylocaproyl polyoxyglycerides, lauroyl polyoxyglycerides, stearoyl polyoxylglycerides and d-α-tocopheryl polyethylene glycol succinate, or combinations thereof. For example, the non-ionic surfactant may be Cremophor RH 40™ (polyoxyl 40 hydrogenated castor oil), Cremophor EL™ (polyoxyl 35 castor oil), Cremophor ELP™ (polyoxyl 35 castor oil), Solutol HS 15™ (macrogol 15 hydroxystearate) or TPGS™ (d-α-tocopheryl polyethylene glycol succinate). For example, the non-ionic surfactant is Cremophor RH 40™ (polyoxyl 40 hydrogenated castor oil), Cremophor EL™ (polyoxyl 35 castor oil) or Cremophor ELP™ (polyoxyl 35 castor oil), and the like Examples of amphoteric surfactants include, but are not limited to, sodium N-dodecyl-γ-alanine, sodium N-lauryl-γ-iminodipropionate, myristoamphoacetate, lauryl betaine, lauryl sulfobetaine, sodium 3-dodecyl-aminopropionate, sodium 3-dodecylaminopropane sulfonate, sodium lauroamphoacetate, cocodimethyl carboxymethyl betaine, cocoamidopropyl betaine, cocobetaine, lauryl amidopropyl betaine, oleyl betaine, lauryl dimethyl carboxymethyl betaine, lauryl dimethyl alphacarboxyethyl betaine, cetyl dimethyl carboxymethyl betaine, lauryl bis-(2-hydroxyethyl)carboxymethyl betaine, stearyl bis-(2-hydroxypropyl)carboxymethyl betaine, oleyl dimethyl gamma-carboxypropyl betaine, lauryl bis-(2-hydroxypropyl)alpha-carboxyethyl betaine, oleamidopropyl betaine, coco dimethyl sulfopropyl betaine, stearyl dimethyl sulfopropyl betaine, lauryl dimethyl sulfoethyl betaine, lauryl bis-(2-hydroxyethyl)sulfopropyl betaine, and combinations thereof.

Examples of cationic surfactants include, but are not limited to, behenyl trimethyl ammonium chloride, bis(acyloxyethyl)hydroxyethyl methyl ammonium methosulfate, cetrimonium bromide, cetrimonium chloride, cetyl trimethyl ammonium chloride, cocamido propylamine oxide, distearyl dimethyl ammonium chloride, ditallowedimonium chloride, guar hydroxypropyltrimonium chloride, lauralkonium chloride, lauryl dimethylamine oxide, lauryl dimethylbenzyl ammonium chloride, lauryl polyoxyethylene dimethylamine oxide, lauryl trimethyl ammonium chloride, laurtrimonium chloride, methyl-1-oleyl amide ethyl-2-oleyl imidazolinium methyl sulfate, picolin benzyl ammonium chloride, polyquatemium, stearalkonium chloride, sterayl dimethylbenzyl ammonium chloride, stearyl trimethyl ammonium chloride, trimethylglycine, and combinations thereof.

Preservatives and Antioxidants

The formulation, according to embodiments of the present invention, may include a preservative, such as those described in *Preservatives for Cosmetics,* 3rd Edition, (Steinberg, D. C. Allured Pub. Corp. 2012). In general, topical formulations require preservation from microbial contamination that may adversely affect the stability of the formulation and infect the user. When present in a formulation, the amount of preservative may be from about 0.001% to about 1% by weight, for example, from about 0.01% to about 0.5% by weight of the total formulation weight. In some instances, it is also advantageous to include an antioxidant to preserve medicaments and excipients present in topical formulations. Some medicaments and excipients are oxygen labile and can undergo oxidation. Antioxidants are included in pharmaceutical formulations to enhance the stability of therapeutic agents that may be susceptible to chemical degradation by oxidation. Antioxidants are typically molecules that exhibit higher oxidative potential than the therapeutic agent or inhibit free radical-induced drug decomposition. When present in a formulation, the amount of antioxidant may be from about 0.001% to about 1% by weight, for example, from about 0.01% to about 0.5% by weight of the total formulation weight.

Examples of preservatives include, but are not limited to, quaternary amines, such as quaternium 15, benzalkonium chloride, cetrimide, benzethonium chloride; and imidizolidinyl urea; organic acids, such as sorbic acid, p-hydroxybenzoic acid, and benzoic acid; parabens, such as methyl paraben, propyl paraben, and butyl paraben; alcohols, such as benzyl alcohol and isopropyl alcohol; phenols, such as triclosan, chlorhexidine, and thimerosal; hydantoin derivatives; chloromethylthiazoline; methylisothiazoline; phenoxyethanol; hexetidine; chlorohexydingluconate; and imidazolidinylurea.

Examples of antioxidants include, but are not limited to, ascorbic acid derivatives (e.g., ascorbic acid, erythorbic acid, sodium ascorbate), thiol derivatives (e.g., thioglycerol, cysteine, acetylcysteine, cystine, dithioerytheritol, dithiothreitol, glutathione), butylated hydroxyanisole (BHA), butylated hydroxytoluene (BHT), sulfurous acid salts (e.g., sodium sulfate, sodium bisulfite, acetone sodium bisulfite, sodium metabisulfite, sodium sulfite, sodium formaldehyde sulfoxylate, sodium thiosulfate), nordihydroguaiaretic acid, and vitamin E (e.g., tocopherols, tocotrienols). Vitamin E refers to a group of eight fat-soluble compounds that include both tocopherols and tocotrienols. Vitamin E has many biological functions; the antioxidant function being one of the most important and best known. It acts as such in the present formulations. Butylated hydroxytoluene (BHT) is a lipophilic organic compound, chemically a derivative of phenol. It acts as an antioxidant and antimicrobial compound in the present formulation.

The formulation disclosed herein may include oxybenzone ((2-hydroxy-4-methoxyphenyl)-phenylmethanone), molecular formula C14H1203, which absorbs UVB and UVA (ultraviolet) radiation. Oxybenzone forms colorless crystals that are readily soluble in most organic solvents and contributes to the photostability of the formulation.

Anti-Foaming Agents

The formulation, according to embodiments of the present invention, may include an anti-foaming agent to facilitate manufacture. Anti-foaming agents dissipate foam by destabilizing the air-liquid interface and allow liquid to drain away from air pockets. When present in a formulation, the amount of anti-foaming agent may be from about 0.01% to about 1% by weight, for example, from about 0.1% to about 0.5% by weight of the total formulation weight.

Examples of anti-foaming agents include, but are not limited to, simethicone, dimethicone, ethanol, and ether.

Emollients, Humectants, and Skin Protectors

The formulation, according to embodiments of the present invention, may include an emollient, a humectant, or a skin protectant. The emollient or humectant may be used to soothe and hydrate the skin. When present in a formulation, the amount of humectant, skin protectant, or emollient may be from about 1% to about 10% by weight, for example, from about 2% to about 5% by weight of the total formulation weight.

Examples of humectants include, but are not limited to, glycerin, sorbitol, triacetin, polyethylene or butylenes glycols, urea, propylene glycol, 1,3-butylene glycol, ethanol, and isopropanol, and combinations thereof. In an embodiment, the humectant may be sorbitol, for example, a 70% aqueous sorbitol solution. Examples of emollients include, but are not limited to, cholesterol and glycerol, myristyl lactate, isopropyl palmitate, light liquid paraffin, cetearyl alcohol, lanolin, lanolin derivatives, mineral oil, petrolatum, cetyl esters wax, cholesterol, glycerol, glycerol monostearate, isopropyl myristate, lecithin, and combinations thereof. Examples of skin protectants include, but are not limited to, vitamin E oil, allatoin, glycerin, zinc oxide, vitamins A, B (e.g., biotin and pantothenic acid), C, E, F, H, and P, and esters thereof.

Penetration Enhancers

The formulation, according to embodiments of the present invention, may include a penetration enhancer. When present in the formulation, the amount of the penetration enhancer may be from about 0.5% to about 10% by weight, for example, from about 0.5% to about 1%, from about 1% to about 2%, from about 2% to about 3%, from about 3% to about 4%, from about 4% to about 5% by weight of the total formulation weight. In an example, the amount of the penetration enhancer may be from about 2% to about 5% by weight of the total formulation weight.

Penetration enhancers may be included in the formulations to optimize transfer of (1S)-1-phenyl-2-pyridin-2-ylethanamine through the stratum corneum and into the dermis/dermatome to provide a local effect. For a discussion of use of penetration enhancers in topical formulations see generally, *Percutaneous Penetration Enhancers* (Eric W. Smith & Howard I. Maibach eds. 1995); Ghosh, T. K. et al. *Pharm. Tech.* 1993, 17, 72; Ghosh, T. K. et al. *Pharm. Tech.* 1993, 17, 62; Ghosh, T. K. et al. *Pharm. Tech.* 1993, 17, 68. The penetration enhancer should be pharmacologically inert, non-toxic, and non-allergenic, have rapid and reversible onset of action, and should be compatible with the formulations described herein.

Exemplary skin penetrating enhancers include alkyl (N,N-disubstituted amino alkanoate) esters, such as dodecyl 2-(N,N dimethylamino) propionate (DDAIP), which is described in U.S. Pat. Nos. 6,083,996 and 6,118,020; a water-dispersible acid polymer, such as a polyacrylic acid polymer, a carbomer (e.g., Carbopol™ or Carbopol 940P™, available from B. F. Goodrich Company (Akron, Ohio)), copolymers of polyacrylic acid (e.g., Pemulen™ from B. F. Goodrich Company or Polycarbophil™ from A. H. Robbins. Richmond, Va.: a polysaccharide gum, such as agar gum, alginate, carrageenan gum, ghatti gum, karaya gum, kadaya gum, rhamsan gum, xanthan gum, and galactomannan gum (e.g., guar gum, carob gum, and locust bean gum), as well as other gums known in the art (see for instance, Industrial Gums: Polysaccharides & Their Derivatives, Whistler R. L., BeMiller J. N. (eds.), 3rd Ed. Academic Press (1992) and Davidson, R. L., Handbook of Water-Soluble Gums & Resins, McGraw-Hill, Inc., N.Y. (1980)); or combinations thereof.

A "cross-linked polyacrylic acid homopolymer" suitable for present purposes is a high molecular weight polymer of acrylic acid cross-linked with polyalkenyl ethers of sugars or polyalcohols such as allyl sucrose, allyl pentacrythiritol, etc., such as Carbopol® 980 NF and the like. Carbopol® 980 NF is commercially available from Lubrizol Advanced Materials, Inc., Cleveland, Ohio. A "cross-linked polyacrylic interpolymer" suitable for present purposes is a high molecular weight copolymer of acrylic acid and C1-C24 alkylmethyacrylates cross-linked with polyalkenyl ethers of sugars or polyalcohols which contain a heterologous polymer, e.g., a block copolymer of polyethylene glycol and a long chain, e.g., C1-C24 alkyl acid ester, such as Carbopol® Ultrez 10 NF, and the like. Carbopol® Ultrez NF is commercially available from Lubrizol Advanced Materials, Inc., Cleveland. Ohio. The interpolymer-homopolymer weight ratio in the formulation may be about 2.5:1.

Other suitable polymeric skin penetrating enhancers are cellulose derivatives, such as ethyl cellulose, methyl cellulose, hydroxypropyl cellulose. Additionally, known transdermal penetrating enhancers can also be added, if desired. Examples of penetration enhancers include, but are not limited to, dimethyl acetamide (DMA), 2-pyrrolidone, N,N-diethyl-m-toluamide (DEET), 1-dodecylazacycloheptane-2-one (Azone™, a registered trademark of Nelson Research), N,N-dimethylformamide (DMF), N-methyl-2-pyrrolidone, calcium thioglycolate and other enhancers such as dioxolanes, cyclic ketones, and their derivatives, transcutol P, ethyl alcohol, isopropyl alcohol, lauryl alcohol, salicylic acid, octolyphenylpolyethylene glycol, polyethylene glycol 400, propylene glycol, N-decylmethylsulfoxide, dimethylsulfoxide (DMSO), and the azacyclo compounds, as disclosed in U.S. Pat. Nos. 4,755,535; 4,801,586; 4,808,414; and 4,920,101.

Also illustrative are a group of biodegradable absorption enhancers which are alkyl N,N-2-(disubstituted amino) alkanoates as described in U.S. Pat. Nos. 4,980,378 and 5,082,866, including: tetradecyl (N,N-dimethylamino) acetate, dodecyl (N,N-dimethylamino) acetate, decyl (N,N- dimethylamino) acetate, octyl (N,N-dimethylamino) acetate, and dodecyl (N,N-diethylamino) acetate.

Examples of skin penetrating enhancers useful in embodiments of the present invention include isopropyl myristate; isopropyl palmitate; dimethyl sulfoxide; decyl methyl sulfoxide; dimethylalanine amide of a medium chain fatty acid; dodecyl 2-(N,N-dimethylamino) propionate or salts thereof, such as its inorganic (e.g., hydrochloric, hydrobromic, sulfuric, phosphoric, and nitric acid addition salts) and organic salts (e.g., acetic, benzoic, salicylic, glycolic, succinic, nicotinic, tartaric, maleic, malic, pamoic, methanesulfonic, cyclohexanesulfamic, picric, and lactic acid addition salts), as described in U.S. Pat. No. 6,118,020; and alkyl 2-(N,N-disubstituted amino)-alkanoates, as described in U.S. Pat. Nos. 4,980,378 and 5,082,866.

Thickening Agents

The formulation, according to embodiments of the present invention, can further include one or more thickening agents. Thickening agents are used to increase viscosity and improve bioadhesive properties. When present in the formulation, the amount of thickening agent may be from about 1% to 10% by weight, for example, from about 2% to about 5% by weight of the total formulation weight.

Examples of thickening agents include, but are not limited to, cellulose, hydroxypropyl cellulose, methyl cellulose, polyethylene glycol, sodium carboxymethyl cellulose, polyethylene oxide, xanthan gum, guar gum, agar, carrageenan gum, gelatin, karaya, pectin, and locust-bean gum, aliginic acid, bentonite carbomer, povidone, and tragacanth.

Bioadhesive Polymers

The formulation, according to embodiments of the present invention, may include a bioadhesive polymer. Besides acting as adhesives, bioadhesive polymers may also be useful to hydrate the skin and enhance its permeability. In addition, bioadhesive polymers may function as thickening agents. Examples of bioadhesive polymers include, but are not limited to, pectin, alginic acid, chitosan, hyaluronic acid, polysorbates, such as polysorbate-20, -21, -40, -60, -61, -65, -80, -81, -85; poly(ethyleneglycol), such as PEG-7, -14, -16, -18, -55, -90, -100, -135, -180, -4, -240, -6, -8, -9, -10, -12, -20, or -32; oligosaccharides and polysaccharides, such as gellan, carrageenan, xanthan gum, gum Arabic, and dextran; cellulose esters and cellulose ethers; modified cellulose polymers, such as carboxymethylcellulose, hydroxyethylcellulose, hydroxypropyl methylcellulose, hydroxyethyl ethylcellulose; polyether polymers and oligomers, such as polyoxyethylene; condensation products of poly(ethyleneoxide) with various reactive hydrogen containing compounds having long hydrophobic chains (e.g., aliphatic chains of about 12 to 20 carbon atoms), for example, condensation products of poly(ethylene oxide) with fatty acids, fatty alcohols, fatty amides, polyhydric alcohols; polyether compounds, such as poly(methyl vinyl ether), polyoxypropylene of less than 10 repeating units; polyether compounds, such as block copolymers of ethylene oxide and propylene oxide; mixtures of block copolymers of ethylene oxide and propylene oxide with other excipients, for example, pluronic lethicin organogel (see *International Journal of Pharmaceutical Compounding* 1997, 1, 71); poly(vinyl alcohol); polyacrylamide; hydrolyzed polyacrylamide; poly(vinyl pyrrolidone); poly(methacrylic acid); poly(acrylic acid) or crosslinked polyacrylic acid, such as carbomer, i.e., a homopolymer of acrylic acid crosslinked with either an allyl ether of pentaerythritol, an allyl ether of sucrose, or an allyl ether of propylene (e.g., Acrisint® 400, 410, or 430 commercially available from 3V Inc. Weehawkin, N.J.); Orabase® (i.e., a mixture of gelatine, pectin and sodium carboxymethyl cellulose in a plasticized hydrocarbon gel, commercially available from Hoyt laboratories, Needhm, Me.); Carafate® (sulfated sucrose and aluminum hydroxide, commercially available from Marion Laboratories, Inc., Kansas City, Mo.). In an example, the block copolymers of ethylene oxide and propylene oxide may be used as bioadhesive polymers.

The formulations, according to embodiments of the present invention, can further include one or more additional ingredients, such as one or more inert carriers, lipid absorbents, viscosity stabilizers, anti-fading agents, stabilizers, moisture absorbents, fragrances, colorants, film-forming materials, and refatting agents, etc. One of ordinary skill in the art would be able to choose such additional excipients based on the physical and chemical properties desired in the final topical formulation. It is understood that a single excipient may have multiple functions and properties.

The above agents may be used in various formulations. Ointments and creams may be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents. Liquid sprays are conveniently delivered from pressurized packs, for example, via a specially shaped closure. Oil-in-water emulsions can also be utilized in the formulations, patches, bandages and articles. These systems are semisolid emulsions, micro-emulsions, or foam emulsion systems. Usually such a system has a “creamy white” appearance. The oleaginous phase may contain, but is not limited to, long-chain alcohols (cetyl, stearyl), long-chain esters (myristates, palmitates, stearates), long-chain acids (palmitic, stearic), vegetable and animal oils and assorted waxes. These can be made with anionic, cationic, non-ionic or amphoteric surfactants, or with combinations especially of the nonionic surfactants.

In an embodiment, Lipoderm® (Professional Compounding Centers of America, Houston, TX) is admixed in the formulations described herein. Alternative ointment bases are known to persons skilled in the art such as Transcutol-P (ethoxydiglycol, commercially available, for example, from Gattefosse, Westwood, N.J.). Sufficient Lipoderm® base is admixed to act as a carrier for the active ingredients of the formulation. Typically, the Lipoderm® base will make up more than about 70% of the total formulation, for example, about 74% of the formulation is the Lipoderm® base. The Lipoderm® base functions as a carrier and enhances penetration through the skin. It is also hypoallergenic and is aesthetically pleasing.

A gel base, according to embodiments of the present invention, may include lecithin, isopropyl palmitate, poloxamer 407, and water. Topical carriers with different viscosities and hand-feel are known to the art. The above active ingredients can be dispersed within the pharmaceutically acceptable carrier in therapeutically effective amounts to treat neuropathies, and the other maladies described above. The topical formulation may include (per gram total weight) from about 15 grams to 30 grams per 100 grams (for example, 20 grams, 25 grams or 30 grams) weight of (1S)-1-phenyl-2-pyridin-2-ylethanamine, a pharmaceutically acceptable salt thereof, a solvate thereof, or a prodrug thereof. Other agents can be added accordingly.

Topical dosage unit forms can be prepared utilizing a variety of techniques that have been described in the art. See, for example, U.S. Pat. Nos. 4,861,800; 4,868,218; 5,128,145; 5,190,763; and 5,242,950; and in the foreign patent documents EP-A 404807; EP-A 509761; and EP-A 593807. A monolithic patch structure can be utilized in which selegiline is directly incorporated into the adhesive and this mixture is cast on to a backing sheet. Alternatively, selegiline as an acid addition salt can be incorporated into a multi-layer patch which effects a conversion of the salt to selegiline-free base, as described, for example, in foreign patent publication EP-A 593807. One can also employ a device using a lyotropic liquid crystalline composition in which, for example, 5-15% of selegiline is combined with a mixture of liquid and sold polyethylene glycols, a polymer, and a non-ionic surfactant, optionally with the addition of propylene glycol and an emulsifying agent. For further details on the preparation of such topical formulations, reference can be made to foreign patent publication EP-A 509761.

As used herein, the terms "drug delivery system," "drug/enhancer composition," or any similar terms refer to a formulated composition containing the drug to be topically delivered in combination with a penetration enhancer. Other pharmaceutically acceptable materials or additives can also be contained in the drug/enhancer composition, such as a diluent, skin-irritation reducing agent, carrier or vehicle, excipient, plasticizer, emollient, or other additive and mixtures thereof provided that such additives do not materially affect the basic and novel characteristics of the matrix patch.

As used herein, the terms "matrix," "matrix system," or "matrix patch" refer to an active permeant or drug dissolved or suspended in a biocompatible polymeric phase, for example, a pressure sensitive adhesive, that can also include other ingredients or in which the enhancer is also dissolved or suspended. This definition is meant to include embodiments wherein such polymeric phase is laminated to a pressure sensitive adhesive or used with an overlay adhesive. A matrix system usually and preferably includes an adhesive layer having an impermeable film backing laminated onto the distal surface thereof and, before topical application, a release liner on the proximal surface of the adhesive. The film backing protects the polymeric phase of the matrix patch and prevents release of the drug and/or enhancer to the environment. The release liner functions similarly to the impermeable backing, but is removed from the matrix patch prior to application of the patch to an application situs. Matrix patches are known in the art of topical drug delivery to routinely contain such backing and release liner components, and matrix patches according to the formulations described herein should be considered to include such backing and release liner or their functional equivalents. U.S. Pat. No. 5,122,383 describes such backing and release liner. A matrix system therefore relates to a unit dosage form of a drug formulation in a polymeric carrier, also containing the enhancer and other components that are formulated for maintaining the drug composition in the polymeric layer in a drug transferring relationship with the derma, i.e., the skin or mucosa. A matrix patch is distinguished from a "liquid reservoir patch," wherein an active permeant or drug is dissolved in a gelled liquid contained in an occlusive device having an impermeable back surface and an opposite surface configured appropriately with a permeable membrane and adhesive for topical application, e.g., U.S. Pat. No. 4,983,395.

A topical formulation may include a conventional aqueous or non-aqueous vehicle, for example, a cream, ointment lotion or paste or in the form of a medicated plaster, patch or membrane.

As used herein, the term "effective amount" of a drug or permeant refers to a non-toxic but sufficient amount of a compound to provide the desired local or systemic effect without adverse side effects. An "effective amount" of permeation enhancer as used herein relates to an amount selected so as to provide the desired increase in membrane permeability and, correspondingly, the desired depth of penetration, rate of administration, and amount of drug.

As used herein, "application situs" relates to a site suitable for topical application with or without the means of a device, patch, or dressing, e.g., the spinal column, behind the ear, on the arm, back, chest, abdomen, leg, top of foot, etc. For example, the cream can be applied to the site of pain or the pain site of spine dermatome(s), e.g., l2-s2 for any leg, knee, or foot neuropathy.

The penetration enhancing compositions of the formulations described herein may constitute a small amount of the formulation or a large amount depending on which topical vehicle is used, which systemically and/or topically active agent is used, and the type of biological effect sought. The amount will be apparent to those of ordinary skill in the art, since the total amount of penetration enhancers will be approximately the same as those of the prior art. For example, when the potency of the penetration enhancement composition is greatly increased, lower quantities can be used.

Chelating Agents

The formulation, according to embodiments of the present invention, may include a chelating agent. The use of chelating agents to stabilize chemicals and drugs in formulations is known. Chelating agents are scavengers for trace amounts of metal ions. Most commonly chelation involves a metal ion. Compounds which have this ability are known as chelating agents or chelating ligands. Many reactions, including many oxidation and decomposition reactions, are catalyzed by trace amounts of metallic ions present in formulations. Many drugs can be degraded through oxidation and hydrolytic reactions which are catalyzed by metal ions. The presence of metallic ions can therefore significantly accelerate the degradation of these drugs. Chelating agents are useful in preventing degradation for drugs in formulations. EDTA (ethylene diamine tetraacetic acid) and its salts are examples of powerful chelating agents. EDTA is known to stabilize drugs in solution by retarding their oxidation. Exemplary chelating agents include EDTA, a salt of EDTA (e.g., the disodium salt of EDTA), deferoxamine, sodium diethyldithiocarbamate, penicillamine, pentetate calcium, a sodium salt of pentetic acid, dimercaptosuccinic acid, triethylenetetramine, nitrilotriacetic acid, trans-diaminocyclohexanetetraacetic acid (DCTA), diethylenetriaminepentaacetic acid, bis(aminoethyl)glycolether-N,N,N',N'-tetraacetic acid, iminodiacetic acid, acetic acid, tartaric acid, fumaric acid, or a salt thereof.

Edetate disodium is also known as the disodium salt of ethylenediaminetetraacetic acid (EDTA). EDTA is available in several salt forms, notably disodium EDTA and calcium disodium EDTA. EDTA is mainly used to sequester metal ions in aqueous solution. In personal care products, it is added to cosmetics to improve their stability toward air. It acts as a chelating agent that helps bind free radicals and impurities in the present formulation.

Buffering Agents

The formulation, according to embodiments of the present invention, may include a buffering agent or pH modifier. There is often an optimum pH range for pharmaceutical formulations, both for compound stability and other factors such as skin permeation and solubility of therapeutic agents. This may require the pH to be adjusted during formulation due to the components of the formulation being too acidic or basic. Buffer systems are often used to maintain the pH within the desired range. Exemplary pH modifiers include acetic acid, adipic acid, ammonium carbonate, ammonium hydroxide, ammonium phosphate, boric acid, citric acid, diethanolamine, fumaric acid, hydrochloric acid, malic acid, nitric acid, propionic acid, potassium acetate, potassium bicarbonate, potassium chloride, potassium citrate, potassium metaphosphate, potassium phosphate, sodium acetate, sodium bicarbonate, sodium borate, sodium carbonate, sodium chloride, sodium citrate, sodium glycolate, sodium hydroxide, sodium lactate, sodium phosphate, sodium proprionate, succinic acid, sulfuric acid, tartaric acid, triethanolamine, or pharmaceutically acceptable salts thereof.

Triethanolamine is an organic compound that is both a tertiary amine and a triol. Like other amines, triethanolamine is a base and functions as a pH modifier in the present formulation. Triethanolamine is used primarily as an emulsifier and surfactant. Triethanolamine neutralizes fatty acids, adjusts and buffers the pH, and solubilizes oils and other ingredients that are not fully soluble in water.

Exemplary Formulations

In an embodiment, a topical formulation may be an oil-in-water emulsion, which may include on a weight basis:

about 0.5 to about 15 percent of lanicemine,
about 0.01 to about 1 percent of a chelating agent,
about 0.15 to about 1.5 percent of a cross-linked polyacrylic acid interpolymer,
about 0.15 to about 1.5 percent of a cross-linked polyacrylic acid homopolymer,
about 2.5 to about 6 percent oxybenzone,
about 0.25 to about 2.5 percent of a an emulsifying agent,
about 5 to about 15 percent of a water-miscible alkylene glycol,
about 10 to about 30 percent of a $C_2$ to $C_3$ alkanol,
about 0.5 to about 2.5 percent of a cosmetic preservative,
about 0.02 to about 2 percent of an antioxidant,
about 0.001 to about 0.1 percent of an emollient,
a buffering agent in an amount sufficient to maintain a pH value of the formulation in the range of about 4.5 to about 6, and
the remainder water.

For example, the topical formulation may include on a weight basis:

about 10 percent of lanicemine,
about 0.05 percent disodium salt of ethylenediaminetetracetic acid,
about 1.25 percent of a cross-linked polyacrylic acid interpolymer,
about 0.5 percent of a cross-linked polyacrylic acid homopolymer,
about 5 percent of oxybenzone,
about 0.5 percent of PEG-40 hydrogenated castor oil,
about 10 percent propylene glycol,
about 10 percent of anhydrous ethanol,
about 9 percent isopropanol,
about 1 percent benzyl alcohol,
about 0.05 percent Vitamin E,
about 1 percent of butylated hydroxytoluene,
about 3 percent isopropyl myristate,
about 1.5 percent triethanolamine, and
the remainder water.

In another example, the topical formulation may include on a weight basis:

about 5 percent of lanicemine,
about 0.05 percent disodium salt of ethylenediaminetetracetic acid,
about 1.25 percent of a cross-linked polyacrylic acid interpolymer,
about 0.5 percent of a cross-linked polyacrylic acid homopolymer,
about 5 percent of oxybenzone,
about 0.5 percent of PEG-40 hydrogenated castor oil,
about 10 percent propylene glycol,
about 10 percent of anhydrous ethanol,
about 9 percent isopropanol,
about 1 percent benzyl alcohol,
about 0.05 percent Vitamin E,
about 1 percent of butylated hydroxytoluene,
about 3 percent isopropyl myristate,
about 1.5 percent triethanolamine, and
the remainder water.

In yet another example, the topical formulation may include on a weight basis:

about 0.5 percent of lanicemine,
about 0.05 percent disodium salt of ethylenediaminetetracetic acid,
about 1.25 percent of a cross-linked polyacrylic acid interpolymer,
about 0.5 percent of a cross-linked polyacrylic acid homopolymer,
about 5 percent of oxybenzone,
about 0.5 percent of PEG-40 hydrogenated castor oil,
about 10 percent propylene glycol,
about 10 percent of anhydrous ethanol,
about 9 percent isopropanol,
about 1 percent benzyl alcohol,
about 0.05 percent Vitamin E,
about 1 percent of butylated hydroxytoluene,
about 3 percent isopropyl myristate,
about 1.5 percent triethanolamine, and
the remainder water.

The oil-in-water emulsions may have cream-like consistency.

In another embodiment, a topical formulation may be a composition, which may include on a weight basis:

about 0.5 to about 15 percent of lanicemine,
a non-basic polymeric skin penetration enhancer present in an amount sufficient to enhance skin penetration of lanicemine, wherein the polymeric skin penetration enhancer is a member of the group consisting of a water-dispersable acid polymer, a polysaccharide gum, or a combination thereof; and a carrier consisting essentially of water; and
a lipophilic solvent which is a combination of one or more aliphatic $C_2$ to $C_8$ alcohols and an aliphatic $C_8$ to $C_{30}$ ester, wherein the lipophilic solvent is present in an amount of about 10 percent to about 40 percent, wherein the ratio of the amount by weight of the aliphatic alcohol to the amount by weight of the ester is in the range of about 7 to about 1.

The non-basic polymeric skin penetration enhancer may be a cross-linked polyacrylic acid interpolymer, a cross-linked polyacrylic acid homopolymer, 2-dimethylaminopropionic acid dodecyl ester or a pharmaceutically acceptable salt thereof, or a combination of two or more thereof. The non-basic skin penetration enhancer may be present in the amount of 1.5 to 1.75 percent based on the weight of the formulation.

The lipophilic solvent may be a combination of ethyl alcohol, isopropyl alcohol, and isopropyl myristate.

The formulation may further include a chelating agent in the amount of 0.01 to 0.1 percent based on the weight of the formulation. The chelating agent may be disodium salt of ethylenediamineteraacetic acid.

The formulation may further include oxybenzone in the amount of 1 to 7 percent based on the weight of the formulation.

The formulation may further include an emulsifying agent in the amount of 0.01 to 1 percent based on the weight of the formulation. The emulsifying agent may be PEG-40 hydrogenated castor oil.

The formulation may further include a water-miscible alkylene glycol in the amount of 7 to 12 percent based on the weight of the formulation. The water-miscible alkylene glycol may be propylene glycol.

The formulation may further include a cosmetic preservative in the amount of 0.05 to 0.15 percent based on the weight of the formulation. The cosmetic preservative may be benzyl alcohol.

The formulation may further include an antioxidant or mixture of antioxidants in the amount of 1 to 1.1 percent based on the weight of the formulation. The antioxidant or mixture of antioxidants may be selected from vitamin E, butylated hydroxytoluene, or a combination thereof.

The formulation may further include a buffering agent in an amount sufficient to maintain a pH value of the formulation in the range of 4.5 to 6. The buffering agent may be triethanolamine.

For example, the formulation may include:

about 10 percent of lanicemine;

about 1.25 percent of a cross-linked polyacrylic acid interpolymer and about 0.5 percent of a cross-linked polyacrylic acid homopolymer;

about 19 percent of a mixture of one or more aliphatic alcohols and about 3 percent of an aliphatic ester;

about 0.05 percent of a chelating agent;

about 10 percent oxybenzone;

about 0.5 percent of an emulsifying agent;

about 10 percent of a water-miscible alkylene glycol;

about 1 percent of a cosmetic preservative;

about 1.05 percent of a mixture of antioxidants;

about 1.5 percent of a pH modifier; and the remainder water.

In another example, the topical formulation may include:

about 5 percent of lanicemine;

about 1.25 percent of a cross-linked polyacrylic acid interpolymer and about 0.5 percent of a cross-linked polyacrylic acid homopolymer;

about 19 percent of a mixture of one or more aliphatic alcohols and about 3 percent of an aliphatic ester;

about 0.05 percent of a chelating agent;

about 5 percent oxybenzone;

about 0.5 percent of an emulsifying agent;

about 10 percent of a water-miscible alkylene glycol;

about 1 percent of a cosmetic preservative;

about 1.05 percent of a mixture of antioxidants;

about 1.5 percent of a pH modifier; and the remainder water.

In yet another example, the topical formulation may include:

about 2.5 percent of lanicemine;

about 1.25 percent of a cross-linked polyacrylic acid interpolymer and about 0.5 percent of a cross-linked polyacrylic acid homopolymer;

about 19 percent of a mixture of one or more aliphatic alcohols and about 3 percent of an aliphatic ester;

about 0.05 percent of a chelating agent;

about 3 percent oxybenzone;

about 0.5 percent of an emulsifying agent;

about 10 percent of a water-miscible alkylene glycol;

about 1 percent of a cosmetic preservative;

about 1.05 percent of a mixture of antioxidants;

about 1.5 percent of a pH modifier; and the remainder water.

The combination of one or more aliphatic alcohols is a mixture of about 10 percent ethanol and about 9 percent isopropanol. The aliphatic ester may be isopropyl myristate. The chelating agent may be disodium salt of ethylenediamineteraacetic acid. The emulsifying agent may be PEG-40 hydrogenated castor oil. The water-miscible alkylene glycol may be propylene glycol. The cosmetic preservative may be benzyl alcohol. The combination of antioxidants may be a combination of about 0.05 percent vitamin E and about 1 percent butylated hydroxytoluene. The buffering agent may be triethanolamine.

Methods of Manufacture

The formulations, according to embodiments of the present invention, may be prepared according to the methods known in the art for preparing emulsions for topical administration. See, for example, methods recited in Gennaro, A. R., Remington: *The Science and Practice of Pharmacy,* 21st edition, Lippincott, Williams & Wilkins (2006). Exemplary preparations are also recited in the Example section below.

The compositions described herein can be made by cold compounding. This method is significant since one or more of the compounds admixed in the topical compositions described herein may be sensitive to heat or other types of energy. Thus, the activity of the composition may be detrimentally affected as a result of the formulation of the compositions in other manners. The ingredients of the topical formulation, according to embodiments of the present invention, can be mixed together, without heating and using a sufficient amount of the carrier to provide a substantially homogeneous cream or gel. In some cases, it may be desired to dissolve, disperse or suspend one or more of the ingredients prior to cold compounding in order to ensure substantially homogeneous distribution of the active ingredients in the composition.

In another method, the components may be separated into those that are water-soluble and those that are oil-soluble. The water-soluble components may be mixed together in one vessel to form a solution and the oil-soluble components can be mixed together in a separate vessel and heated (e.g., 70° C. to 80° C.) to form a solution. The two solutions may then be mixed, and the mixture may be allowed to cool. This method only requires two beakers and a heating apparatus. Homogenation is achieved using a high-shear rate blender or other suitable apparatus. The appropriate droplet size is achieved by standard adjustment of the shear rate during high-speed mixing followed by droplet size analysis as described in Gennaro, A. R., Remington: *The Science and Practice of Pharmacy,* 21st edition, Lippincott, Williams & Wilkins (2006) and Allen & Terence, Particle Size Measurement 483 (4th ed. 1990). Suitable equipment and methods for preparing formulations, according to embodiments of the invention, such as high-shear rate blenders are described in 2 Remington: *The Science and Practice of Pharmacy* 1509-1515 (Alfonso R. Gennaro ed., 19th ed. 1995) (updated in Gennaro, A. R., Remington: *The Science and Practice of Pharmacy,* 21st edition, Lippincott, Williams & Wilkins (2006)). Methods for preparation of emulsions for topical administration, suitable for preparing formulations, according to embodiments of the present invention, are also described in Bernard Idson, Pharmaceutical Emulsions in 1 *Pharmaceutical Dosage Forms: Disperse Systems* 199 (Herbert A. Lieberman et al. eds. 1988).

The formulations, according to embodiments of the present invention, may then be packaged and stored according to methods known in the art. For example, see the packaging procedures described in 1 Remington: *The Science and Practice of Pharmacy* 390-391 (Alfonso R. Gennaro ed., 19th ed. 1995—updated in Gennaro, A. R., Remington: *The Science and Practice of Pharmacy,* 21st edition, Lippincott, Williams & Wilkins (2006)). If desired, the formulations may be sterilized according to methods known in the art, for example, the methods described in 2 Remington: *The Science and Practice of Pharmacy* 1463-1486 (Alfonso R. Gennaro ed., 19th ed. 1995-updated in Gennaro, A. R., Remington: *The Science and Practice of Pharmacy,* 21st edition, Lippincott, Williams & Wilkins (2006)).

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 15% to about 30%" should be interpreted to include not only the explicitly recited values of about 15% to about 30%, but also include individual values and subranges within the indicated range. Thus, included in this numerical range are individual values such as 15, 16, 17, 18, 19, 20, 21, 22, 23, 24, 25, 26, 27, 28, 29, and 30, and sub-ranges such as from 15 to 25, 20 to 25, and from 20 to about 30, etc. This same principle applies to ranges reciting only one numerical value. Furthermore, such an interpretation should apply regardless of the breadth of the range or the characteristics being described.

Application

The formulations, according to embodiments of the present invention, may be administered to mammals, including humans, pets, and livestock and other farm animals and sport animals. The methods described herein are primarily used on but not limited to humans, but may also include pets, such as dogs and cats; farm mammals, such as horses, cows, pigs, and sheep; and laboratory animals, such as monkeys, guinea pigs, rats, rabbits, and mice.

The site of application is dependent on several factors including, but not limited to, the amount of drug to be delivered, the extent of enhancement required, the side effects manifested and the time of application. Thus, another important facet of the methods described herein is the use of these formulations, alone or in combination with other drugs, or to apply such formulations, or topical products in general, specifically to the soles of the feet, the palms of the hands or other immune-privileged sites of the body. Also, the drugs, formulations, or products may be administered later in the day or at night when the permeability at the site of application is higher.

The general mode of action of the formulation is through "topical administration." As used herein, the term "topical administration" or "topical application" refers to directly layering or spreading upon epidermal tissue, especially outer skin or membrane, including but not limited to the skin or membrane of cutaneous, mucosal or oral, vaginal, rectal, ocular, or nasal surfaces or cavities. The formulation is topically administered to a subject in an amount and duration sufficient to prevent or relieve pain associated with any cause, including, but not limited to, neuropathic inflammation, and acute and chronic peripheral neuropathy.

Methods described herein may also involve the topical application of a formulation described herein to areas of the skin in the vicinity of tissue that suffers from neuropathic pain. In particular, the formulations and methods described herein are useful on the patients' extremities such as the peripheral appendages (e.g., fingers, toes, hands, arms, leg, and feet) and general areas of pain (e.g., torso, back, shoulder, neck, head) where the neuropathic pain, including peripheral neuropathy, is often the most pervasive, or the dermatome site along the spine. The site can also be in the vicinity of tissue that has undergone traumatic injury such as surgery, amputation, lesion, infection or other such injury. The methods and formulations described herein can also be applied to the specific ganglia that mediate pain to the spinal column and to the spine itself. Specific dermatomes are involved for the correct application of the formulations described herein for neuropathic analgesia.

Administration to the subject is performed in accordance with that mode which is most amenable to the topically acceptable form chosen. For example, gels, lotions, creams, and ointments may be administered by spreading. Because hydrated skin is more permeable than dry skin, the dosage form may be modified or an occlusive dressing may be applied to facilitate absorption. Also contemplated by the formulations and methods described herein are slow-release or sustained-release forms, whereby a relatively consistent level of the formulation is provided over an extended period.

The formulation, according to embodiments of the present invention, can be topically administered to intact skin by a medical professional or by the patient by simple mechanical rubbing into the application site, or by applying a transdermal patch to the site. In applying these formulations to the skin, for maximum effectiveness and increased absorption, the area to which the formulation is administered is covered with a hot, dampened cloth for approximately one minute. The area is then allowed to dry for a few seconds. Next, the formulation is rubbed on to the complete target area of the skin (the painful area) and gently, but firmly, massaged in with the fingertips until all visible gel or cream has been absorbed.

The surface area that is covered by the topical formulation following application must be sufficient to provide for the desired amount of agent administration, and in representative embodiments ranges from about 1 to 200 $cm^2$, and in many embodiments from about 10 to 180 $cm^2$, for example, from about 10 to 100 $cm^2$, e.g., 10, 20, 30, 40, or 50 $cm^2$. For example, in the case of diabetic neuropathy, the subject may apply the invention topical treatment over the entire foot and lower leg, or the arm/forearm. In some embodiments, the period of time that the formulation is maintained at the site of application does not exceed about 48 hours, and in representative embodiments does not exceed about 24 hours. However, the period of time during which the preparation is maintained at the application site is, in some embodiments, at least about 15 to 30 minutes, usually at least about 1 hour. In practicing the subject methods, a given dosage of the topical formulation may be applied a single time or a plurality of times over a given time period, e.g., the course of the pain condition being treated, where the dosing schedule when a plurality of formulations are administered over a given time period may be daily, weekly, biweekly, monthly, etc. Treatment may be applied as needed and for such length as determined by the healthcare provider, e.g., physician, or on the level of pain.

In an embodiment, a suitable amount of a formulation described herein may be applied one to six times daily as needed to relieve pain and other symptoms of neuropathy.

For example, the formulation is applied two to four times daily, as needed for pain. A sufficient amount is applied to cover the area afflicted by the neuropathy with a thin layer of the formulation and the formulation is rubbed into the skin until little or no residue remains on the skin. Treatment begins initially to treat acute symptoms but may be continued indefinitely to relieve pain, prevent symptoms of neuropathy from returning and possibly restore some nerve and/or skin function. The application frequency and volume of the formulation may decrease over time, but not necessarily. With gels, creams, or ointments, typically 1 to 10 applications may be needed per day, for example, 2, 3 or 4 applications per day, or as many as needed. Generally, the greater the level of pain the greater the number of applications.

The methods described herein also encompass topical administration of formulations in a physiologically acceptable topical vehicle and in an amount and duration sufficient to provide an antineuropathic response. Hence the terms "transdermal," "topical," and "transmucosal" are used interchangeably unless specifically stated otherwise. Similarly, the terms "skin," "derma," "epidermis," "mucosa," and the like shall also be used interchangeably unless specifically stated otherwise.

A specific mode of administration of the formulation, according to embodiments of the present invention, is through "topical administration." As used herein, "transdermal" or "percutaneous" delivery relates to delivery of a drug by passage into and through the skin or mucosal tissue. This mode of action is restricted to the region of the dermis where the drug application has occurred. In using the topical route of administration, the amount of formulation absorbed systemically is generally minimal. The vehicle can, however, allow the active ingredients to efficiently penetrate tissues when applied topically and can allow increased concentrations of (1S)-1-phenyl-2-pyridin-2-ylethanamine and all added agents in the formulations described herein. Topical administration of the formulations described herein is directed to cutaneous surfaces. The formulation can be applied topically on a subject in an amount and duration sufficient to prevent or relieve pain associated with any cause, including, but not limited to, neuropathic inflammation, and acute and chronic peripheral neuropathy.

A subject can be treated in accordance with the formulations described herein by administering (1S)-1-phenyl-2-pyridin-2-ylethanamine, a pharmaceutically acceptable salt thereof, a solvate thereof, or a prodrug thereof suspended in or admixed with a physiologically suitable topical vehicle and manually applied or sprayed (either with a manually-actuated pump or with the aid of a suitable pharmaceutically-acceptable propellant) onto the surface area in need of treatment. For example, the formulation may be applied by topical massage. Suitable formulations for topical application of drugs are known to those of ordinary skill in the art and can be routinely selected.

The amount of the formulation to be applied may vary depending on the choice of the vehicle. For example, when the formulation is administered by spraying an alcoholic liquid solution of the active ingredient, the total volume in a single dose can be very low. Conversely, when the formulations described herein are administered in a topical cream, the total volume can be higher. The vehicle selected and its manner of application is preferably chosen in consideration of the needs of the patient and the preferences of the administering medical practitioner.

In an embodiment, the formulations disclosed herein may be contained in a patch that is applied adjacent to the area of skin to be treated. As used herein a "patch" includes at least the formulation and a covering layer, such that, the patch can be placed over the area of skin to be treated. The patch may be designed to maximize drug delivery through the stratum corneum and into the epidermis or dermis, and to minimize absorption into the circulatory system, reduce lag time, promote uniform absorption, and reduce mechanical rub-off.

Examples of patches suitable for use with the formulations, according to embodiments of the present invention, include (1) the matrix-type patch; (2) the reservoir-type patch; (3) the multi-laminate drug-in-adhesive type patch; (4) the monolithic drug-in-adhesive type patch; and (5) hydrogel patch. See generally, Ghosh, T. K.; Pfister, W. R.; Yum, S. I. *Transdermal and Topical Drug Delivery Systems, Interpharm Press, Inc*. p. 249-297. These patches are known in the art and available commercially.

In general, the active ingredient will include from about 0.5 percent to about 40 percent by weight of the patch, for example, from about 10 percent to about 30 percent, from about 15 percent to about 25 percent, or from about 18 percent to about 22 percent by weight of the patch.

The patches for use with formulations, according to embodiments of the present invention, can be manufactured, packaged, stored and labeled according to standard procedures. For example, see the procedures described in Bova et al., *Product Development and Technology Transfer for Transdermal Therapeutic Systems in Transdermal Controlled Systemic Medications* 379-396 (Y. W. Chien ed. 1987); J. W. Dohner, *Development of Processes and Equipment for Rate Controlled Transdermal Therapeutic Systems in Transdermal Controlled Systemic Medications* 349-364 (Y. W. Chien ed. 1987); H-M. Wolf et al., *Development of Processes and Technology for Adhesive-Type Transdermal Therapeutic Systems in Transdermal Controlled Systemic Medications* 365-378 (Y. W. Chien ed. 1987).

Topical or transdermal application of the formulations described herein is useful for relieving pain, inflammation and irritation associated with skin diseases and disorders. Painful lesions develop, for example, from viral infections, i.e., herpes zoster, skin cancers and genetic disorders. Acute post-operative or surgical pain may be reduced or even eliminated as may pain associated with chronic disorders, such as diabetic peripheral polyneuropathy. The methods described herein may also provide one or more of the beneficial effects described above. In addition, methods described herein may provide some additional beneficial effects due to one or more of the ingredients contained in the pharmaceutically acceptable carrier such as described above, e.g., the return of sensory perception at the application site.

Dosage

The amount of the formulation, according to embodiments of the present invention, that is necessary to produce a therapeutic effect at an affected area may be based on various factors, including the strength of the active ingredients, the ingredients admixed, the pain type and intensity, or related to, the location and size of the area and the relative condition that is to be treated, side effect profiles, or may be based on factors targeting consensus or generalized populations. For example, the amount of the formulation needed to treat severe pain is likely to be greater than the amount of the formulation needed to treat mild to moderate forms of the affliction. In addition, an acute condition will likely require medication for less time or shorter duration than a chronic condition, or alternatively, lesser frequency of application. Individual sensitivities will also influence the dosage amounts administered to a particular subject. A determination of the appropriate dose is within the skill of one of ordinary skill in the art given the factors herein. The dosage range may be determined by considering the amount of the active ingredients in percentage, and the surface area to be treated. The concentration of the active ingredients in the formulation may be from about 0.001% to about 50% of the total formulation. Additional compounds, such as those listed above that reduce or may reduce neurotoxicity of the active ingredients, may be added from about 0.001% to about 50% of the total formulation. In accordance with the formulations and methods described herein, the foregoing doses can be readily optimized following the teachings herein, based on known pharmacological protocol, by those of ordinary skill in the art, with no more than routine optimization. The preferred lower limit for drug delivery may be that necessary to bring about an anti-neuropathic effect. The preferred upper limit may be less than that amount which produces untoward side effects.

Although not crucial, the dilution and/or formulation of the active ingredients of the formulations described herein, in a physiologically acceptable topical vehicle, may be important and useful in providing the final dosage concentration. The formulations may be supplied in solid, semi-solid or liquid forms, including tablets, capsules, powders, liquids, and suspensions. The formulations described herein may therefore encompass concentrated forms for subsequent dilution before use or sale. The formulations may include any physiologically acceptable topical excipients including, but not limited to, gels, lotions, creams, ointments, and liquids, as further elaborated herein.

Selection of the appropriate dosage of the formulation, according to embodiments of the present invention, for the application site is an important consideration. The rate of topical analgesic administration from the topical formulation or patch is a function of skin permeability, and skin permeability has been shown to vary between anatomical sites depending on the thickness of the stratum corneum. For example, the permeability, in general, increases in order from planter foot arch, lateral ankle, palm, ventral forearm, dorsal forearm, back, chest, thigh, abdomen, scalp, axilla, forehead, and scrotum. See R. C. Wester. & H. I. Maibach "Regional variation in Percutaneous Absorption in Percutaneous Absorption, Mechanism, Methodology", *Drug Delivery* 111-119 (R. L. Bronaugh & H. I. Maibach eds., 2nd ed. 1989). The dosages and dosing frequency would be determined by a trained medical professional and would depend upon many factors such as application site and size and the severity of the indication.

In general, a dosage from about 0.05 or 0.1 mg/kg to about 5 g/kg subject body weight may be utilized to carry out the method of treating neuropathic pain, according to embodiments of the present invention, for example, from about 1 mg/kg to about 1 mg/kg per application. In an embodiment, approximately 0.5 g to about 2 g of the topical preparation may be applied per administration, with about 10-30% of the preparation being the active ingredient. Generally, about 0.1 g/$cm^2$ of skin area to about 5 g/$cm^2$, for example, 0.1 mg/$cm^2$ to about 2 g/$cm^2$ of the formulation, according to embodiments of the present invention, may be administered to and around the application site. For example, the dosage form may be from 0.1 mg/$cm^2$ to about 1 g/$cm^2$, or 0.5 mg/$cm^2$ to about 0.5 g/$cm^2$ per application.

The therapeutically effective dosage of the active ingredient, the use of which is in the scope of embodiments of the present invention, will vary somewhat from compound to compound, and patient to patient, and will depend upon the condition of the patient and the route of delivery. Exemplary duration of the treatment may be one to ten dosages per day for a period of one to several days, one to several weeks, such as two to three weeks, one or several months, or until the condition is controlled or treated. In some embodiments lower doses given less frequently can be used to prevent or reduce the incidence of recurrence of the condition being treated.

As used herein, topical delivery also includes numerous different systems for the topical delivery of active agents known in the art. Topical delivery systems include but are not limited to passive devices such as drug-in-adhesive topical patches and "active" topical technologies such as iontophoresis, electroporation, sonophoresis, magnetophoresis, microneedle devices and those devices that use thermal energy to make the skin more permeable.

Topical drug delivery devices are available from the 3M Drug Delivery Systems Division (St. Paul, Minn., USA), Noven Pharmaceuticals, Inc. (Miami, Fla., USA), ImaRx (Tucson, Ariz., USA), Elan Corporation (Dublin, Ireland), Novosis AG (Miesbach, Germany), Ultrasonic Technologies (St. Albans, Vt., USA), Antares Pharma (Exton, Pa., USA), Altea Therapeutics (Tucker, Ga., USA), lomed, Inc. (Salt Lake City, Utah, USA), MacroChem Corp (Lexington, Mass., USA), Sontra Medical Corporation (Franklin, Mass., USA), Vyteris, Inc. (Fair Lawn, N.J., USA), BioChemics, Inc. (Danvers, Mass., USA), A. P Pharma (Redwood, City, Calif., USA), MIKA Pharma GmbH (Limburgerhof, Germany), NexMed, Inc. (Robbinsville, N.J., USA), Encapsulation Systems, Inc. (Springfield, Pa., USA), Acrux Ltd (Elgin, Ill., USA), Jenapharm GmbH (Berlin, Germany), Norwood Abbey (Victoria, Australia), Novavax (Columbia, Md., USA), Genetronics Biomedical Corporation (San Diego, Calif., USA), Adherex Technologies (Research Triangle Park, N.C., USA), and AlphaRx (Ontario, Canada).

When a patch is used to administer a formulation, according to embodiments of the present invention, the dosage to achieve pain relief is determined by the active surface area of the medicated portion of the patch in direct contact with the skin. Several dosage strengths are advantageous depending upon the severity of the wound. In general, a physician can begin dosing with a low or intermediate strength patch and then, depending upon the effectiveness, adjust the dosage up or down by prescribing a patch of higher or lower active concentration or a patch of larger or smaller surface area, or, in some cases, multiple patches. The formulation, according to embodiments of the present invention, may include from about 0.5 percent to about 20 percent by weight of the patch, for example, from about 5 percent to about 25 percent by weight of the patch. For matrix (drug-in-adhesive) type patches, the formulations, according to embodiments of the present invention, may include from about 0.5 percent to about 20 percent by weight of the patch. For patches including a hydrogel, the formulations, according to embodiments of the present invention, may include from about 0.5 percent to about 10 percent by weight of the patch. Fresh patches may be administered multiple times per day, but a fresh patch may be administered about every 18 to about every 48 hours, or daily.

Topical drug delivery using patch technology may be accomplished by using a covering element in the form of a topical patch device that is attached to the host at the desired drug delivery site. A typical topical patch structure includes a drug-in-adhesive layer sandwiched between an impermeable backing and a release liner. At the time of use, the release liner is easily removed so that the patch can be attached to the host, adhesive side down. The impermeable backing thus traps the drug-in-adhesive layer between the backing and the attachment site of the host. Over time, the drug penetrates into the host, or is topically active, in accordance with the desired therapeutic treatment. Optionally, the drug-in-adhesive formulation may include one or more compounds known as penetration enhancers that increase the delivery of the drug to the subject. See, for example, U.S. Pat. No. 6,627,216.

Some examples of topical patch technology include but are not limited to those described in U.S. Pat. Nos. 6,592,893; 6,267,983; 6,238,693; 6,211,425; 6,159,497; 6,153,216; 5,948,433; 5,508,035; 5,284,660; 4,942,037; and 4,906,463.

Iontophoresis, an active topical technology, uses low voltage electrical current to drive charged drugs through the skin. Those molecules with a positive charge are driven into the skin at the anode and those with a negative charge are driven into the skin at the cathode. See, for example, U.S. Pat. No. 6,622,037. Additional examples of iontophoretic delivery devices for the topical delivery of active agents include but are not limited to those described in U.S. Pat. Nos. 6,564,903; 5,387,189; 5,358,483; 5,356,632; 5,312,325; 5,279,544; 5,167,479; 5,156,591, 5,135,479; 5,088,977; 5,057,072; 5,053,001; and 4,942,883.

Electroporation is similar to iontophoresis in that it uses electrical fields to aid in transport of molecules across the stratum corneum. However, rather than driving the molecules through the skin, electroporation uses high-voltage electric field pulses to create transient pores which permeabilize the stratum corneum (SC) (Prausnitz et al., *Proc. Natl. Acad. Sci.* 1993, 90, 10504-10508; Murthy et al. *J. Control. Release* 2004, 98, 307-315; U.S. Pat. No. 5,947,921)). Examples of electroporation technology for topical delivery include but are not limited to U.S. Pat. Nos. 6,692,456; 6,564,093; 6,517,864; 6,512,950; 5,968,006; and 5,749,847.

The technique of sonophoresis utilizes ultrasound to disrupting the stratum corneum, creating cavitations which disorder the lipid bilayers resulting increased drug transport. Although a variety of ultrasound conditions have been used for sonophoresis, the most commonly used conditions correspond to frequencies in the range of between one MHz and three MHz, and intensity in the range of between above zero and two W/cm$^2$ (U.S. Pat. No. 4,767,402). Other devices use low frequency ultrasound that is less than one MHz (U.S. Pat. No. 6,234,990). Other examples of sonophoretic devices include but are not limited to those described in U.S. Pat. Nos. 6,491,657; 6,487,447; 6,190,315; 6,041,253; 5,947,921; 5,906,580; and 5,445,611.

An additional method used to facilitate the transport of compounds across the stratum corneum is the use of thermal energy. Examples of the use of thermal energy technology to facilitate transport of compounds across the stratum corneum include but are not limited to those described in U.S. Pat. Nos. 6,780,426; 6,613,350; 6,465,006; 6,284,266; 6,261,595; 6,048,337; 4,898,592; 4,685,911; and 4,230,105.

Magnetophoresis, the use of magnetic energy, is an additional method used to increase drug transport across the stratum corneum. Some examples of magnetophoretic delivery devices include but are not limited to those disclosed in U.S. Pat. Nos. 6,564,093; 5,983,134; 5,947,921; 4,702,732.

Microneedles or microstructured arrays are used to create micropores in the stratum corneum to aid in the flux of drugs across the skin. Examples of microneedle technology includes but is not limited to the disclosure in U.S. Pat. No. 6,331,310 and H. Sebastien, et al, *J. Pharm. Sci.* 1998, 87, 922-925.

Method of Treating Neuropathic Pain

The formulations and methods, according to an embodiment, are effective to induce local anaelgesia and to treat neuropathic pain. As used herein, the term "neuropathic pain" refers to neuropathic-pain syndromes, that is, pain due to lesions or dysfunction in the nervous system. As used herein, the term "local" refers to the limited area near the site of administration, generally the nerves at or near skin including the epidermis, the dermis, the dermatomes and the like. Local analgesics including (1S)-1-phenyl-2-pyridin-2-ylethanamine reversibly block nerve conduction near their site of administration, thereby producing temporary loss of sensation and/or relief of pain or neuropathy in a limited area (the nerves of the dermis or dermatome (area of the skin associated with dorsal roots from the spine)), with no or limited systemic penetration beyond the skin.

The formulations and methods, according to embodiments of the present invention, can be used to treat or prevent pain related to or induced by the following diseases, trauma, or conditions: general neuropathic conditions, such as peripheral neuropathy, phantom limb pain, reflex-sympathetic dystrophy, causalgia, syringomyelia, and painful scar; specific neuralgias at any location of the body; back pain; diabetic neuropathy; alcoholic neuropathy; metabolic neuropathy; inflammatory neuropathy; chemotherapy-induced neuropathy, herpetic neuralgias; traumatic odontalgia; endodontic odontalgia; thoracic-outlet syndrome; cervical, thoracic, or lumbar radiculopathies with nerve compression; cancer with nerve invasion; traumatic-avulsion injuries; mastectomy, thoracotomy pain; spinal-cord-injury; stroke; abdominal-cutaneous nerve entrapments; tumors of neural tissues; arachnoiditis; stump pain; fibromyalgia; regional sprains or strains; myofascial pain; psoriatic arthropathy; polyarteritis nodosa; osteomyelitis; burns involving nerve damage; AIDS-related pain syndromes; connective tissue disorders, such as systemic lupus erythematosis, systemic sclerosis, polymyositis, and dermatomyositis; and inflammatory conditions, such as acute inflammation (e.g., trauma, surgery and infection) or chronic inflammation (e.g., arthritis and gout).

Topical application of the formulation, according to embodiments of the present invention, may be useful for relieving pain, inflammation and irritation associated with skin diseases and disorders, such as psoriasis, pruritus, and lesions. Painful lesions develop, for example, from viral infections, skin cancers and genetic disorders. Topical application of the formulation provides relief from pain associated with wounds, insect and animal bites, abrasions and burns, including those resulting from over-exposure to the sun, chemicals, radiation or chemotherapeutic agents. Acute post-operative or surgical pain can be reduced or even prevented, as can pain associated with chronic disorders, such as arthritis.

In some embodiments, the methods described herein can provide a treatment by applying the formulations described herein to an affected area of a subject with diabetic polyneuropathy. In other embodiments, the methods described herein can include treating peripheral neuropathy, including the step of topical administration of a pharmaceutical formulation including lanicemine in a topical vehicle to the affected area of a subject in need of such treatment.

Thus, the methods and formulations, according to embodiments of the present invention, can be effective for neuropathies, particularly peripheral neuropathies, associated with diseases such as: uremia; childhood cholestatic liver disease; chronic respiratory insufficiency; alcoholic polyneuropathy; multiple organ failure; sepsis; hypoalbuminemia; eosinophilia-myalgia syndrome; hepatitis; *por-*

*phyria*; hypoglycemia; vitamin or nutritional deficiency (e.g., B-12 deficiency); chronic liver disease; primary biliary cirrhosis; hyperlipidemia; leprosy; Lyme disease; herpes zoster; Guillain-Barre syndrome; chronic inflammatory demyelinating polyradiculoneuropathy; sensory perineuritis; HIV or acquired immunodeficiency syndrome (AIDS)-associated neuropathy; Sjogren's syndrome; primary vasculitis (such as polyarteritis nodosa); allergic granulomatous angiitis; hypersensitivity angiitis; Wegener's granulomatosis; Raynaud's Phenomenon, including CREST syndrome, autoimmune diseases such as erythromatosis (systemic lupus erythematosis); rheumatoid arthritis or other rheumatoid diseases; mixed connective tissue disease; scleroderma; sarcoidosis; vasculitis; systemic vasculitides; acute tunnel syndrome; pandysautonomia; primary, secondary, localized or familial systemic amyloidosis; hypothyroidism; chronic obstructive pulmonary disease; acromegaly; malabsorption (sprue, celiac disease); carcinomas (sensory, sensorimotor, late and demyelinating); lymphoma (including Hodgkin's), polycythemia vera; multiple myeloma (lytic type, osteosclerotic, or solitary plasmacytoma); benign monoclonal gammopathy; macroglobulinemia; cryoglobulinemia; tropical myeloneuropathies; herpes simplex infection; cytomegalovirus infection; cranial nerve palsies; drug-induced neuropathy; industrial neuropathy; lymphomatous neuropathy; myelomatous neuropathy; multi-focal motor neuropathy; immune-mediated disorders, chronic idiopathic sensory neuropathy; carcinomatous neuropathy; acute pain autonomic neuropathy; alcoholic neuropathy; compressive neuropathy; vasculitic/ischaemic neuropathy; mono- and polyneuropathies; and diabetes.

Genetically acquired neuropathies suitable for treatment by the methods and formulations described herein include, without limitation: peroneal muscular atrophy (Charcot-Marie-Tooth Disease) hereditary amyloid neuropathies, hereditary sensory neuropathy (type I and type 11), porphyric neuropathy, hereditary liability to pressure palsy, Fabry's Disease, adrenomyeloneuropathy, Riley-Day Syndrome, Dejerine-Sottas neuropathy (hereditary motor-sensory neuropathy-Ill), Refsum's disease, ataxia-telangiectasia, hereditary tyrosinemia, anaphalipoproteinemia, abetalipoproteinemia, giant axonal neuropathy, metachromatic leukodystrophy, globoid cell leukodystrophy, and Friedrich's ataxia.

In other embodiments, formulations described herein are directed to treatment of neuropathic pain, especially pain caused by nerve injury or sympathetically mediated pain. Sympathetically mediated pain (SMP) is a type of pain in which over activity of the sympathetic nervous system plays a crucial role. It includes the syndromes of reflex sympathetic dystrophy (RSD), causalgia, neuropathic pain secondary to nerve injury, and pain from neuromas. It encompasses all neurogenic pain that is not central and is related to a nerve injury regardless of the cause. Neuropathic pain syndromes include, without limitation (other than the neuropathies described herein), allodynia, various neuralgias such as post herpetic neuralgia and trigeminal neuralgia, phantom limb pain, hyperpathia, hyperesthesia, hyperalgesia, dyesthesia, paresthesia, anesthesia delorosa, deafferatation pain, and complex regional pain syndromes (CRPS), such as reflex sympathetic dystrophy (RSD) and causalgia. Non-limited examples include low back pain, sciatica, Guillain-Barre Syndrome, post-surgical traumatic neuropathy, and diabetic peripheral polyneuropathy.

The embodiments of the present invention are further illustrated by the following non-limiting examples.

EXAMPLES

1. Materials (1S)-1-phenyl-2-pyridin-2-ylethanamine, a pharmaceutically acceptable salt thereof, a solvate thereof, or a prodrug thereof are obtained as described above.

All other materials were obtained from various chemical suppliers.

2. HPLC Analytical Methods for Cream Assay and Permeation Studies

A. Chromatographic Conditions.

An isocratic reversed-phase HPLC system is used to determine the stability and photostability of the ketoprofen formulations. The HPLC instrument is Agilent 1100. NovaPak® 4.6×300 mm C18 column from Waters is used. The mobile phase consisted of a mixture of formic acid buffer (0.025 M) adjusted to pH 2.3 with hydrochloric acid and acetonitrile (50:50). The flow rate is 1.0 ml/min. Detection is accomplished at 220 nm and 254 nm. The volume of injection is set to 25 μl. The concentration ranges for the calibration curves of (1S)-1-phenyl-2-pyridin-2-ylethanamine and the run time for the samples are adjusted accordingly.

B. Sample Preparation.

For the stability studies, approximately 75 or 50 mg of sample for formulations containing 5% and 10% lanicemine, respectively, is weighed directly in 25 ml volumetric flasks. Approximately 20 ml of mobile phase is added to each flask, then vortexed for 3 min, filled to volume with mobile phase and shaken well.

For photostability studies, approximately 150 mg of sample is weighed in porcelain crucible which was spread evenly across the bottom of the vessel. The crucibles are passed under a UV curing system (Fusion UV Curing LC6B with H Lamp, Fusion Systems, Rockville, Md.) on a conveyor belt for 5 min. which moves at a speed of 7 to 8 passes per min. The intensity of the UV light is measured using a digital illuminometer (Model YF-1065F) whose value ranges consistently from 250 to 300 foot candles. In comparison, the intensity of light in the laboratory is only 2 to 3 foot candles. The composition in the crucible is then washed 5 times with mobile phase into 150 ml beakers and transferred to 50 ml volumetric flasks with triplicate washings. The flasks are vortexed for 3 min, filled to volume with mobile phase and shaken well. The diluted samples are centrifuged for 10 min prior to filling the HPLC vials for analysis.

3. Methodology for Assessing the Permeation of (1S)-1-phenyl-2-pyridin-2-ylethanamine Dermatomed cadaver skin (Science Care, Aurora, Colo.) is used without further treatment. Porcine skin (Lampire Biological Laboratories, Pipersville, Pa.) is dermatomed to standard thickness. Permeation studies are performed using modified Franz cells with an exposed skin membrane surface area of approximately 1.3 $cm^2$ at 37° C. with sampling times at 2, 4, and 22 hours and assayed by HPLC. Each Franz cell receives one small aliquot of cream sample of approximately 100 mg, lightly spread on the skin membrane surface using a glass rod and covered with a cover disc to prevent moisture loss. The receptor phase contained pH 7.4 phosphate buffer.

4. Methodology for Assessing the Photodegradation of (1S)-1-phenyl-2-pyridin-2-ylethanamine Preparations are exposed to an ultra-high intensity UV light source (~300 lux) for 5 minutes or 10 minutes. At this exposure level human skin would readily burn. Aliquots of the exposed cream are assayed for (1S)-1-phenyl-2-pyridin-2-ylethanamine content using the HPLC procedure described above.

5. Methodology for Assessing Freeze/Thaw Stability

Samples are stored at 0° C. for 24 hours followed by thawing at 25° C. for 24 hours. Samples are observed for phase separation after each cycle. For each sample, five cycles are assessed.

6. Exemplary Formulations

Exemplary formulations are listed in Table 1.

TABLE 1

| Component | Sample 1 | Sample 2 | Sample 3 | Sample 4 |
|---|---|---|---|---|
| Lanicemine | 10 | 5 | 3 | 0.5 |
| Disodium EDTA, USP | 0.05 | 0.05 | 0.05 | 0.05 |
| Purified Water, USP | q.s. | q.s. | q.s. | q.s. |
| Carbopol ® 980, NF | 0.5 | 0.5 | 0.5 | 0.5 |
| Carbopol ® Ultrez 10, NF | 1.25 | 1.25 | 1.25 | 1.25 |
| PEG-40 Hydrogenated Castor Oil, NF | 0.5 | 0.5 | 0.5 | 0.5 |
| Vitamin E USP | 0.05 | 0.05 | 0.05 | 0.05 |
| Ethanol USP, anhydrous | 10 | 10 | 10 | 10 |
| Propylene glycol, USP | 10 | 10 | 10 | 10 |
| Isopropanol, USP | 10 | 10 | 10 | 10 |
| Isopropyl Myristate, USP | 3 | 3 | 3 | 3 |
| Benzyl Alcohol, NF | 1 | 1 | 1 | 1 |
| Oxybenzone, USP | 5 | 5 | 5 | 5 |
| Butylated Hydroxytoluene, NF | 1 | 1 | 1 | 1 |
| Triethanolamine | 1.5 | 1.5 | 1.5 | 1.5 |
| pH | 5 | 5 | 5 | 5 |

The preferred formulations have relatively high skin permeation within the first 2 hours and excellent continued permeation for up to 24 hours.

7. Preparation of Gel Base

Mixture A: In a suitable vessel, EDTA (5 g) is dissolved in purified water (5,500 g) with stirring. To the solution of EDTA in water, Carbopol 980 NF (50 g) is added with vigorous stirring until completely dissolved. Subsequently, Carbopol Ultrez (125 g) is added with vigorous stirring until completely dissolved.

Mixture B: In a separate vessel, Cremophor (50 g), α-tocophenol acetate oil (5 g), ethyl alcohol (1 g), propylene glycol (1,000 g), isopropyl alcohol (900 g), isopropyl myristate (300 g), and benzyl alcohol (100 g) are mixed together with stirring. To this mixture, oxybenzone (500 g) and BHT (100 g) are added at 30-40° C. with stirring until completely dissolved.

Mixture B is then added to mixture A with vigorous stirring. To the combined mixture, a solution of triethanolamine (100 g) in purified water (115 g) is added with vigorous stirring. A solution of triethanol amine (50 g) in purified water (100 g) is added until the pH was between 4.5-5.5 or purified water (100 g) is added if the pH was already between 4.5-5.5. The mixture is homogenized with a high viscosity mixer. This gel base is used to formulate the therapeutic agents into final formulations.

8. Preparation of Gel Base without Benzyl Alcohol

Mixture A: In a suitable vessel, EDTA (5 g) is dissolved in purified water (5,500 g) with stirring. To the solution of EDTA in water, Carbopol 980 NF (50 g) is added with vigorous stirring until completely dissolved. Subsequently, Carbopol Ultrez (125 g) is added with vigorous stirring until completely dissolved.

Mixture B: In a separate vessel, Cremophor (50 g), α-tocophenol acetate oil (5 g), ethyl alcohol (1 g), propylene glycol (1,000 g), isopropyl alcohol (900 g), and isopropyl myristate (300 g) are mixed together with stirring. To this mixture, oxybenzone (500 g) and BHT (100 g) are added at 30-40° C. with stirring until completely dissolved. Mixture B is then added to mixture A with vigorous stirring. To the combined mixture, a solution of triethanolamine (100 g) in purified water (115 g) is added with vigorous stirring. A solution of triethanol amine (50 g) in purified water (100 g) is added until the pH is between 4.5-5.5 or purified water (100 g) is added if the pH is already between 4.5-5.5. The mixture is homogenized with a high viscosity mixer. This gel base is used to formulate the therapeutic agents into final formulations.

9. Preparation of Cream Base

To make 100 mL of a cream base, Carbomer NF, isopropyl myristate, disodium EDTA, sodium methyl paraben, and sodium propyl n parabens are mixed using a suitable mixer as described in U.S. Pat. No. 6,083,996. This cream base was used to formulate the therapeutic agents into final formulations.

10. Preparation of Cream Base with DDAIP

To make 100 mL of a cream base, the hydrochloride or sulfuric acid salt of 2-dimethylaminopropionic acid dodecyl ester, isopropyl myristate, disodium EDTA. Sodium methyl paraben and sodium propyl n-paraben are mixed using a suitable mixer as described in U.S. Pat. No. 6,083,996. This cream base was used to formulate the therapeutic agents into final formulations.

11. Preparation of Ointment

To prepare 50 g of drug product 0.5 g of micronized ketoprofen was dissolved in 15 g of ethyl alcohol (95%) and mixed with a formulation of Examples 1-4 (32.5 g) with vigorous mixing. To the resulting product triethanolamine (0.75 g) was added and the pH adjusted to between 5.3 and 5.5 under vigorous mixing.

12. Preparation of Topical Spray

The topical formulations prepared in this example are clear, sprayable, aqueous ethanolic solutions including lanicemine. The aqueous spray solutions in this example contain lanicemine in the range of about 1 to about 10 percent by weight, preferably about 5 percent by weight. The aqueous spray solution also contains lauryl lactate ($C_{15}H_{30}O_3$) in the range of about 1 to about 5 percent by weight, lactic acid ($C_3H_6O_3$) in the range of about 0.5 to about 5 percent by weight, glyceryl monolaurate ($C_{15}H_3O_4$) in the range of about 2 to about 5 percent by weight. The aqueous spray solution optionally includes propylene glycol ($C_3H_8O_2$) in the range of about 5 to about 30 percent by weight. The remainder of the solution is constituted by water and ethanol in the range of about 0.3:1 to about 2.6:1 water: ethanol. The aqueous spray solution can also include a nonionic surfactant having a hydrophile-lipophile balance (HLB) value of at least 12. The nonionic surfactant can be polyethylene glycol ether of cetyl alcohol represented by the formula $(CH_3(CH_2)_{14}CH_2(OCH_2CH_2)_nOH$, where n has an average of 10, and having a HLB value of about 15.7.

The aqueous spray solution is prepared by first combining lanicemine with lauryl lactate, lactic acid, and glyceryl monolaurate, and dissolving the mixture by gradual addition, at ambient temperature, of alternating aliquots of water and ethanol, followed by the addition of propylene glycol. The nonionic surfactant is added, if desired, to the mixture prior to the addition of water and ethanol.

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

13. Neuropathic Pain Treatment in Animal Model

[Describe Animal Models Used to Treat Neuropathic Pain]

Those skilled in the art will recognize, or be able to ascertain using no more than routine experimentation, numerous equivalents to the specific procedures described herein. Such equivalents are considered to be within the scope of this invention and are covered by the following claims. For example, pharmaceutically acceptable salts other than those specifically disclosed in the description and Examples herein can be employed. Furthermore, it is intended that specific items within lists of items, or subset groups of items within larger groups of items, can be combined with other specific items, subset groups of items or larger groups of items whether or not there is a specific disclosure herein identifying such a combination.

What is claimed is:

1. A pharmaceutical formulation, comprising:

a pharmaceutically acceptable salt of (1S)-1-phenyl-2-pyridin-2-ylethanamine, or a prodrug (1S)-1-phenyl-2-pyridin-2-ylethanamine; and a pharmaceutically acceptable topical carrier, wherein the pharmaceutically acceptable salt is a salt of a fatty acid selected from a C6-C12 carboxylic acid, a C13-C21 carboxylic acid, and a C22-C30 carboxylic acid.

2. The pharmaceutical formulation of claim 1, wherein the fatty acid is a saturated fatty acid selected from caprylic acid, capric acid, lauric acid, stearic acid, arachidic acid, behenic acid, lignoceric acid, and cerotic acid.

3. The pharmaceutical formulation of claim 1, wherein the fatty acid is an unsaturated fatty acid.

4. The pharmaceutical formulation of claim 3, wherein the unsaturated fatty acid is a cis-unsaturated fatty acid selected from myristoleic acid, palmitoleic acid, sapienic acid, oleic acid, linoleic acid, -linoleic acid, arachidonic acid, eicosapentaenoic acid, erusic acid, and docosahexaenoic acid.

5. The pharmaceutical formulation of claim 3, wherein the unsaturated fatty acid is a trans-unsaturated fatty acid selected from elaidic acid, vaccenic acid, and linoelaedic acid.

6. The pharmaceutical formulation of claim 1, wherein the fatty acid is a linear chain carboxylic acid comprising an even number of carbon atoms selected from caprylic acid, capric acid, lauric acid, stearic acid, arachidic acid, behenic acid, lignoceric acid, cerotic acid, myristoleic acid, palmitoleic acid, sapienic acid, oleic acid, linoleic acid, α-linoleic acid, arachidonic acid, eicosapentaenoic acid, erusic acid, and docosahexaenoic acid.

7. The pharmaceutical formulation of claim 1, wherein the fatty acid is a linear chain carboxylic acid comprising an odd number of carbon atoms selected from a pentadecanoic acid and a heptadecanoic acid.

8. The pharmaceutical formulation of claim 1, wherein the fatty acid is an omega-3 fatty acid selected from α-linoleic acid, stearidonic acid, natural eicosatetraenoic acid, eicosapentaenoic acid, clupanodonic acid, tetracosapentaenoic acid, tetracosahexaenoic acid, and docosahexaenoic acid.

9. The pharmaceutical formulation of claim 2, wherein the naturally occurring fatty acid is an omega-6 fatty acid selected from linoleic acid, γ-linoleic acid, dihomo-γ-linoleic acid, arachidonic acid, tetracosatetraenoic acid, tetracosapentaenoic acid, and osbond acid.

10. The pharmaceutical formulation of claim 1, comprising a prodrug of (1S)-1-phenyl-2-pyridin-2-ylethanamine represented by Chemical Formula 2:

Chemical Formula 2

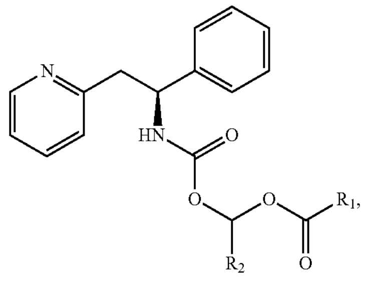

or a pharmaceutically acceptable salt thereof, wherein, in Chemical Formula 2, $R_1$ is a lipophilic moiety derived from a C1-C30 carboxylic acid having formula $R_1$—$CO_2H$, and $R_2$ is H or a C1-C10 unsubstituted or substituted hydrocarbon group.

11. The pharmaceutical formulation of claim 10, wherein $R_1$ is a lipophilic moiety derived from a C8-C30 carboxylic acid having formula $R_1$—$CO_2H$.

12. The pharmaceutical formulation of claim 10, wherein $R_2$ is selected from the group consisting of a C1-C10 alkyl group, a C1-C10 alkenyl group, and a C1-C10 alkynyl group.

13. The pharmaceutical formulation of claim 1, further comprising an analgesic, an anesthetic, a medicinal agent selected from the group consisting of an antifungal agent, an antibiotic, an antiseptic, an anti-inflammatory agent and a neuroprotective agent, or a combination thereof.

14. A method for treating neuropathic pain, comprising administering to a patient in need of such treatment a therapeutically effective amount of a pharmaceutical formulation, comprising:

a pharmaceutically salt of (1S)-1-phenyl-2-pyridin-2-ylethanamine, or a prodrug (1S)-1-phenyl-2-pyridin-2-ylethanamine; and a pharmaceutically acceptable topical carrier, wherein the pharmaceutically acceptable salt is a salt of a fatty acid selected from a C6-C12 carboxylic acid, a C13-C21 carboxylic acid, and a C22-C30 carboxylic acid.

15. The method of claim 14, wherein the neuropathic pain is peripheral neuropathy, mononeuropathy, mononeuritis multiplex, polyneuropathy, autonomic neuropathy, neuritis, phantom limb pain, reflex-sympathetic dystrophy, causalgia, syringomyelia, painful scar, specific neuralgias at any location of the body, back pain, diabetic neuropathy, alcoholic neuropathy, metabolic neuropathy, inflammatory neuropathy, chemotherapy-induced neuropathy, herpetic neuralgias, traumatic odontalgia, endodontic odontalgia, thoracic-outlet syndrome, cervical, thoracic or lumbar radiculopathy with nerve compression, cancer with nerve invasion, traumatic-avulsion injury, mastectomy, thoracotomy pain, spinal-cord-injury, stroke, abdominal-cutaneous nerve entrapments, tumors of neural tissues, arachnoiditis, stump pain, fibromyalgia, regional sprains or strains, myofascial pain, psoriatic arthropathy, polyarteritis nodosa, osteomyelitis, burns involving nerve damage, AIDS-related pain syndromes, sunburn associated syndromes, or connective tissue disorders.

* * * * *